US011650186B2

(12) United States Patent
Ferracane et al.

(10) Patent No.: US 11,650,186 B2
(45) Date of Patent: May 16, 2023

(54) THERMOPLASTIC FILMS AND BAGS WITH COLOR CHANGING INDICATORS AND METHODS OF MAKING THE SAME

(71) Applicant: THE GLAD PRODUCTS COMPANY, Oakland, CA (US)

(72) Inventors: Dean A. Ferracane, Willowbrook, IL (US); Jeffrey S. Stiglic, Willowbrook, IL (US); Jessica Greer, Willowbrook, IL (US); Robert T. Dorsey, Willowbrook, IL (US)

(73) Assignee: The Glad Products Company, Oakland, CA (US)

( * ) Notice: Subject to any disclaimer, the term of this patent is extended or adjusted under 35 U.S.C. 154(b) by 787 days.

(21) Appl. No.: 16/566,606

(22) Filed: Sep. 10, 2019

(65) Prior Publication Data

US 2020/0103383 A1    Apr. 2, 2020

Related U.S. Application Data

(60) Provisional application No. 62/740,303, filed on Oct. 2, 2018.

(51) Int. Cl.
*G01N 31/22* (2006.01)
*G01N 21/78* (2006.01)
(Continued)

(52) U.S. Cl.
CPC .............. *G01N 31/225* (2013.01); *A61L 9/01* (2013.01); *A61L 9/012* (2013.01); *B32B 1/00* (2013.01);
(Continued)

(58) Field of Classification Search
CPC ... A61L 9/01; A61L 9/012; B32B 1/00; B32B 2307/758; B32B 2439/06; B32B 27/08; B32B 27/18; B32B 7/027; B65D 31/02; B65D 33/004; G01N 31/22; G01N 31/221; G01N 31/222; G01N 31/223; G01N 31/225; G01N 21/77; G01N 21/78; G01N 21/783; G01N 21/80; G01N 21/81; Y10T 436/25875
(Continued)

(56) References Cited

U.S. PATENT DOCUMENTS 4,875,914 A    10/1989    Wireman
5,053,339 A    10/1991    Patel
(Continued)

*Primary Examiner* — Maureen Wallenhorst
(74) *Attorney, Agent, or Firm* — Keller Preece PLLC

(57) ABSTRACT

The present disclosure relates to a thermoplastic film that includes a layer of thermoplastic material and a color indicator applied to the thermoplastic material. The color indicator can be configured to change color in response to a trigger. For example, the color indicator can change color (e.g., change from a first color to a second color) in response to a color change trigger, such as exposure to malodor particles, absorption of moisture, a length of time, or as a result of oxidation. In one or more embodiments, the thermoplastic film further includes an odor control component configured to mask, neutralize, or otherwise control malodors. The color indicator can change its color appearance as the odor control component performs to control any present malodors, thus signaling the performance of the odor control component.

20 Claims, 15 Drawing Sheets

(51) Int. Cl.
*B32B 7/027* (2019.01)
*A61L 9/01* (2006.01)
*A61L 9/012* (2006.01)
*B32B 1/00* (2006.01)
*B32B 27/08* (2006.01)
*B65D 30/08* (2006.01)
*B65D 33/00* (2006.01)

(52) U.S. Cl.
CPC .............. *B32B 7/027* (2019.01); *B32B 27/08* (2013.01); *B65D 31/02* (2013.01); *B65D 33/004* (2013.01); *G01N 21/78* (2013.01); *G01N 31/22* (2013.01); *G01N 31/222* (2013.01); *B32B 2307/758* (2013.01); *B32B 2439/06* (2013.01)

(58) Field of Classification Search
USPC ........ 116/201, 206; 436/163, 164, 165, 167, 436/169, 181; 422/400, 401, 402, 420, 422/425, 83, 86, 88, 555
See application file for complete search history.

(56) References Cited

U.S. PATENT DOCUMENTS

| | | | |
|---|---|---|---|
| 7,837,663 | B2 | 11/2010 | MacDonald et al. |
| 8,784,779 | B2 | 7/2014 | Schaeffer-Korbylo et al. |
| 9,926,519 | B2 | 3/2018 | Rees |
| 10,549,888 | B2 * | 2/2020 | Jean-Mary .............. B31B 70/74 |
| 2005/0112085 | A1 * | 5/2005 | MacDonald ....... B01J 20/28007 424/76.1 |
| 2005/0143505 | A1 | 6/2005 | Rosekelly et al. |
| 2006/0291756 | A1 * | 12/2006 | Thomas ............. B65D 33/2525 206/524.4 |
| 2009/0067760 | A1 * | 3/2009 | Shelley ................. B65D 81/28 264/238 |
| 2011/0164834 | A1 * | 7/2011 | Stiglic ................ B31B 70/8135 383/75 |
| 2013/0331308 | A1 | 12/2013 | Rees et al. |
| 2017/0008261 | A1 * | 1/2017 | Jean-Mary .............. B32B 27/08 |
| 2017/0305104 | A1 * | 10/2017 | Wilcoxen ............... B32B 27/08 |
| 2019/0099973 | A1 * | 4/2019 | Borchardt .......... B31B 70/8135 |

* cited by examiner

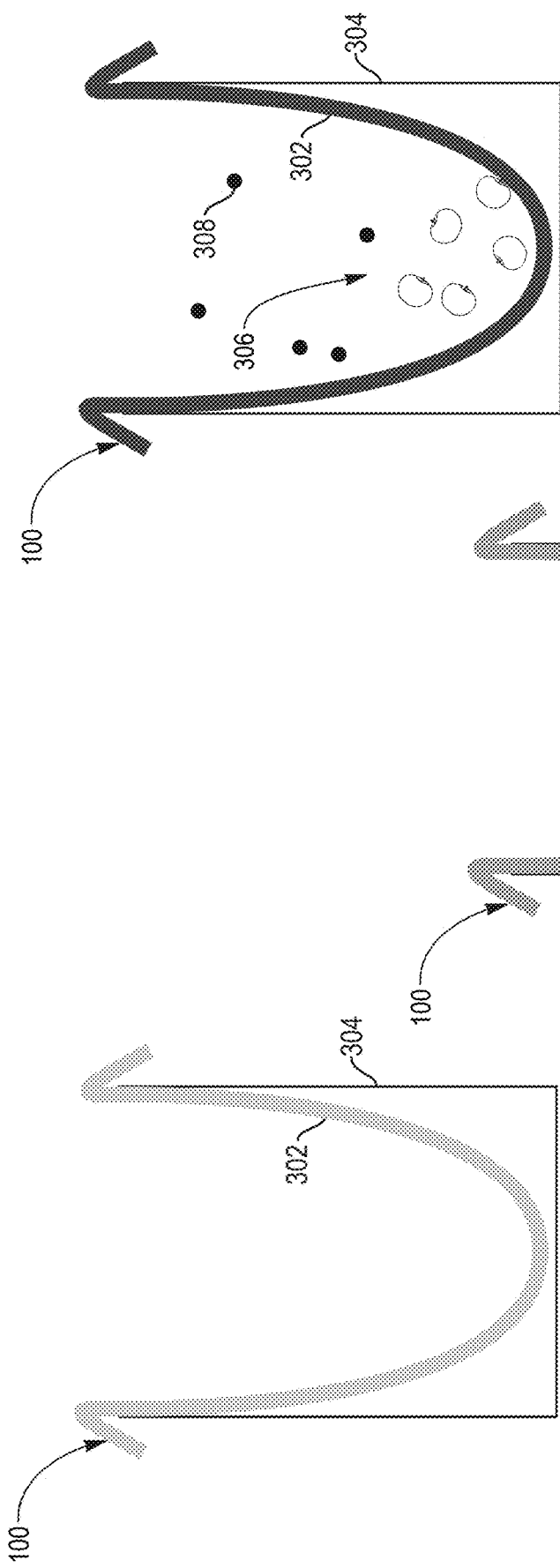

THERMOPLASTIC FILMS AND BAGS WITH COLOR CHANGING INDICATORS AND METHODS OF MAKING THE SAME

CROSS REFERENCE TO RELATED APPLICATIONS

This application claims the benefit of, and priority to, U.S. Provisional Patent Application No. 62/740,303, filed Oct. 2, 2018, which is incorporated herein by reference in its entirety.

BACKGROUND

Thermoplastic films are a common component in various commercial and consumer products. For example, grocery bags, trash bags, sacks, and packaging materials are products that are commonly made from thermoplastic films. Additionally, feminine hygiene products, baby diapers, adult incontinence products, and many other products include thermoplastic films to one extent or another.

In regard to trash bags formed from thermoplastic films, responding to malodors from materials placed in the trash bags (e.g., trash) is a significant concern. In particular, each article of trash placed into a trash bag may function as a source of malodor, and many articles of trash may produce detectably potent malodors. Users may desire to avoid interacting with (i.e., smelling) malodors produced by trash by replacing the trash bag before the malodors become noticeable. In some instances, a given article of trash may produce a malodor that grows in potency over time (e.g., as the article of trash decays) until it creates a detectable stench within the trash bag and, possibly, the surrounding area. In other instances, the quantity of malodor-producing articles of trash placed within the trash bag during its use may produce a combination of malodors potent enough to create such a detectable smell. In either case, a user of the trash bag may not be aware of the malodors emanating from the bag (i.e., may not be aware of the need to replace the trash bag) until the malodor becomes detectable. In other words, a malodor may operate as the sole indicator of its presence, forcing the user to smell the malodor before replacing the trash bag.

Some trash bag manufacturers may apply one or more odor control components (e.g., a fragrance or neutralizing component) to the trash bag to help mask, neutralize, or otherwise control the malodors produced by the trash within the trash bag. However, such trash bags typically have a limited supply of odor control component. Consequently, a trash bag may exhaust the supply of odor control component, allowing any excessive malodors to create a detectable stench. A user may not know that the odor control component has been exhausted until the resulting stench has been detected.

Further, trash bags with odor control components typically maintain operation of the odor control components (i.e., that the odor control components are working to control malodors) undisclosed. Thus, even if the odor control components are effective in controlling the malodors, there may be confusion regarding such effectiveness.

Accordingly, there are a number of considerations to be made in thermoplastic films and responding to odors with thermoplastic films.

SUMMARY

One or more embodiments of the present invention provide benefits and/or solve one or more of the foregoing or other problems in the art with thermoplastic films and bags that include a color indicator that operates to provide a visual indication of the presence of malodor. For example, in one or more embodiments, a thermoplastic film includes a layer of thermoplastic material and a color indicator applied to the layer of thermoplastic material. The color indicator can operate to change its color appearance in response to a color change trigger. To illustrate, the color indicator can change from a first color to a second color after exposure to malodor particles. Additionally, or alternatively, the color indicator can change its color appearance upon absorbing moisture or as a result of oxidation. By changing its color appearance, the color indicator can indicate, to a user, the presence of malodor within the thermoplastic film (and a need to replace the thermoplastic film). In one or more embodiments, the thermoplastic film further includes an odor control component configured to mask, neutralize, or otherwise control malodors. The color indicator can change its color appearance as the odor control component operates to control any present malodors, thus further indicating the performance of the odor control component.

One or more embodiments include a film comprising a first layer of thermoplastic material and a color indicator applied to the first layer of thermoplastic material. The color indicator is configured to change a color appearance in response to a color change trigger.

One or more further embodiments include a thermoplastic bag comprising a first sidewall and a second sidewall opposite the first sidewall and joined with the first sidewall along a first side edge, an opposite second side edge, and a bottom edge. The thermoplastic bag also includes a color indicator applied to at least one of the first sidewall or the second sidewall. The color indicator is configured to change a color appearance in response to a color change trigger.

Additionally, one or more embodiments include a method of manufacturing thermoplastic bags having color indicators. The method involves providing a thermoplastic film and providing a color indicator. In particular, the method involves applying the color indicator to the thermoplastic film. The color indicator is configured to change a color appearance in response to a color change trigger. The method also involves forming the thermoplastic film into a bag.

Additional features and advantages of exemplary implementations of the present invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims or may be learned by the practice of such exemplary embodiments as set forth hereinafter.

BRIEF DESCRIPTION OF THE DRAWINGS

In order to describe the manner in which the above recited and other advantages and features of the present disclosure can be obtained, a more particular description of the present disclosure briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the present disclosure and are not therefore to be considered to be limiting of its scope, the present disclosure will be described and explained with additional specificity and detail through the use of the accompanying drawings in which:

FIGS. 3A-3C illustrate a sequence wherein a color indicator changes a color appearance in the presence of malodor particles in accordance with one or more embodiments;

DETAILED DESCRIPTION

Figure 1:
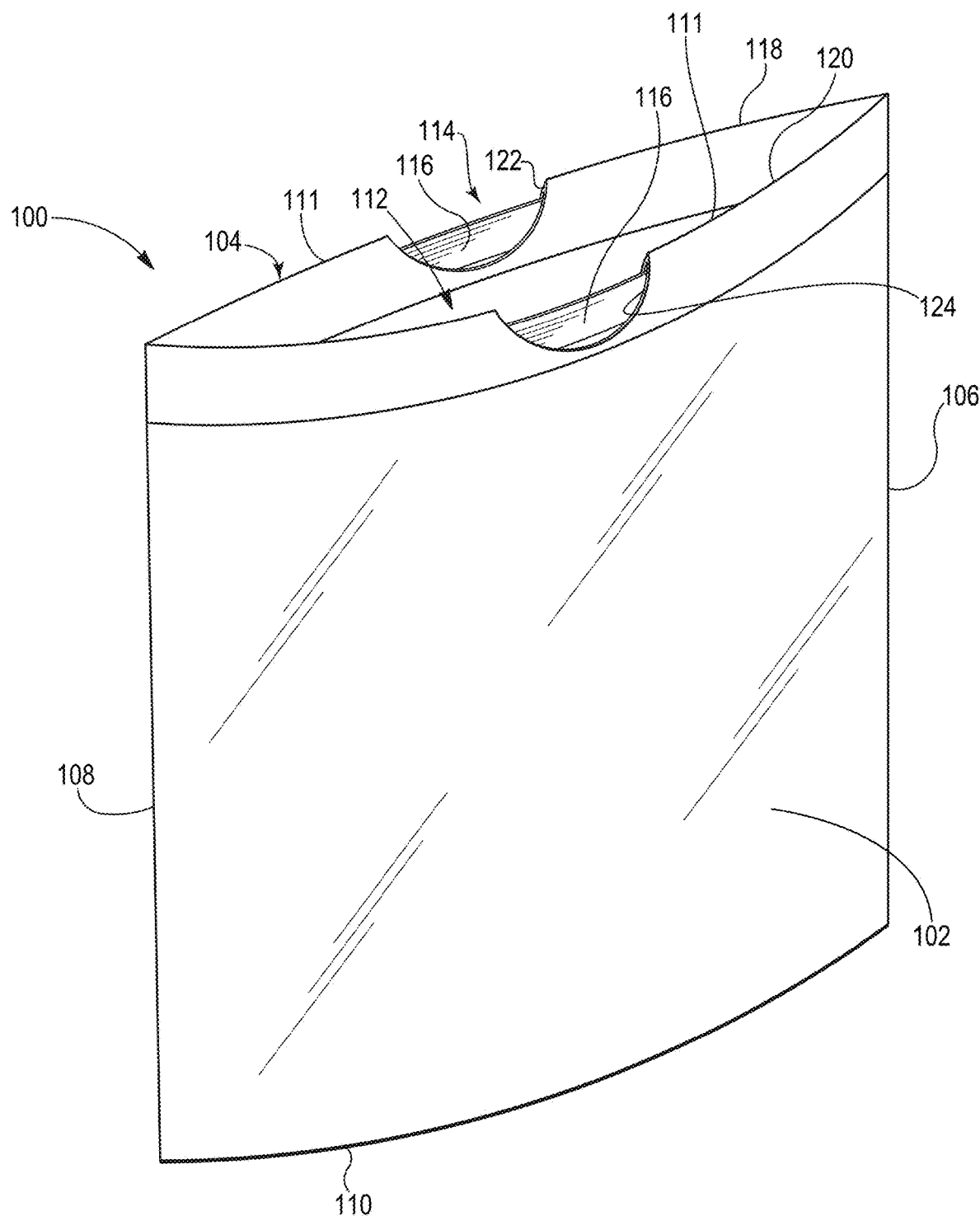
FIG. 1 illustrates a perspective view of a thermoplastic bag in accordance with one or more embodiments.

One or more embodiments of the present disclosure include a color indicator that operates to change a color appearance in response to a color change trigger. For example, in one or more embodiments, a thermoplastic film or bag comprises a color indicator. The color indicator is configured to change its color appearance in response to a color change trigger. For example, the color indicator can change from a first color to a second color after being exposed to particles (e.g., malodor particles) having a chemical structure that provides the particles with a particular pH level. Additionally, or alternatively, the color indicator can change its color appearance after having absorbed moisture or as a result of oxidation. In one or more embodiments, the thermoplastic film or bag further comprises an odor control component and the color indicator can change its color appearance as the odor control component performs to control any present malodors.

In one or more embodiments, the color indicator is co-extruded with the thermoplastic material so that the color indicator is embedded into the material itself. In some embodiments, the color indicator is applied to the thermoplastic material after extrusion (e.g., using a liquid or powder application). For example, the color indicator can be disposed onto a surface of the thermoplastic material (e.g., in a pattern—such as a strip, a series of dots, or other predetermined pattern—or as a complete layer covering the surface), within a hem of a thermoplastic bag, or between a first layer and a second layer of the thermoplastic material.

As mentioned above, the color indicator is configured to change its color appearance in response to a color change trigger. For example, in one or more embodiments, the color indicator is configured to change its color appearance when exposed to malodor particles. In some embodiments, the color indicator is configured to change its color appearance based on the chemical structure of the malodor particles. To illustrate, the color indicator can be configured to change its color appearance based on a chemical structure that provides the malodor particles with a particular pH level. In one or more embodiments, the color indicator is configured to change its color appearance based on exposure to moisture. In further embodiments, the color indicator is configured to change its color appearance as a result of oxidation. By changing its color appearance, the color indicator can provide a visual indication of levels of malodor contained within the thermoplastic film or bag. This improvement allows the thermoplastic film or bag to inform a user of the need to replace the film or bag.

Additionally, as mentioned above, one or more embodiments further include an odor control component applied to the thermoplastic film or bag. In particular, the odor control component is configured to control malodors to which the thermoplastic film or bag is exposed. For example, in one or more embodiments, the odor control component is configured to release an encapsulated odor control active from an encapsulant when exposed to malodor particles. The color indicator can be configured to change its color appearance as the odor control component performs to control malodor (e.g., releases the odor control active). Thus, the color indicator can provide a visual indication that confirms, to a user, effective performance of the odor control component.

As illustrated by the foregoing discussion, the present disclosure utilizes a variety of terms to describe features and benefits of one or more embodiments. Additional detail is now provided regarding the meaning of these terms.

As used herein, the term "color indicator" refers to a structure or compound that can exhibit various visible appearances. In particular, a color indicator refers to a compound configured to transition between various colors. A color indicator can change color to indicate that a particular event has occurred. In one or more embodiments, the event comprises the passage of a predetermined amount of time. In other embodiments, a color indicator can be configured to change its color appearance based on the presence of a high level of malodor or the performance of an odor control component.

In one or more embodiments, the color indicator changes its color appearance in response to a color change trigger. As used herein, a "color change trigger" refers to the occurrence of an event. In particular, a color change trigger refers to an event that causes the color indicator to change its color appearance. For example, a color change trigger can include moisture absorption, oxidation, passage of time, or exposure to one or more particles (e.g., malodor particles) having a chemical structure that provides the particles with a particular pH level.

Additionally, as used herein, the term "odor control component" refers to a structure or compound configured to control malodor. In particular, an odor control component can include an odor control active configured to control malodor.

As used herein, the term "odor control active" refers to a composition that effects (e.g., changes and/or masks) odors in at least one manner. For example, the odor control active can absorb (e.g., foul smell odors) and/or may include fragrance materials. Furthermore, the odor control active can mask (e.g., cover up) and/or neutralize malodors. As used herein the term "neutralize" or any of its derivative terms refers to an ability of a compound or product to reduce or eliminate malodorous compounds. Odor neutralization may be partial, affecting only some of the malodorous compounds in a given context, or affecting only a portion of a malodorous compound. A malodorous compound may be neutralized by chemical reaction resulting in a new chemical entity, by sequestration, by chelation, by association, or by any other interaction rendering the malodorous compound less malodourous or non-malodorous.

For example, the odor control active can include one or more gaseous, liquid, colloidal suspension, and/or solid substances. In one or more embodiments, the odor control active includes a volatile fragrance material (i.e., a fragrance material capable of being transported to the olfactory system). For example, the odor control active can include top, middle, and/or bottom notes of a fragrance composed of aromatic materials and other functional groups (e.g., ketones, aldehydes, alcohols, etc.). As used herein the term "fragrance" refers to any mixture or composition comprising one or more perfume raw materials with or without one or more carrier solvents configured to emit a pleasant odor.

In one or more embodiments, the odor control active comprises functional perfume raw materials (e.g., neutralizing chemistries—such as reactive aldehydes—or perceptual modifiers—such as receptor blockers). As used herein the term "perfume" refers to a compound utilized for its appealing odor. Compounds may have a pleasing odor without being used as a perfume in the context of this disclosure.

In further embodiments, the odor control active comprises one or more neutralizing agents. For example, in some embodiments, the odor control active includes oxidizing chemistries (e.g., peroxides, hypochlorous acid, chlorine, ozone, sodium perborate, etc.).

In some embodiments, the odor control active comprises antimicrobial agents. For example, the odor control active can include zinc pyrithione ("ZPT") and/or copper pyrithione ("CPT")). In some embodiments, the odor control active comprises vapor phase antimicrobials. For example, the odor control active can comprise essential oils (e.g., thymol, lemongrass, tea tree, etc.), chlorine dioxide and/or ethylene oxide.

Moreover, the odor control active can include one or more of desiccant materials (e.g., a hygroscopic substance, such as calcium oxide or silica gel, that has a high affinity for water and is used as a drying agent), deodorizing agents (i.e., deodorizing compositions with a deodorizing effect on offensive odors such as that associated with activated nitrogen compound, activated sulfur compounds, etc.), and functional nanoparticles. In yet further embodiments, the odor control active can include a trapping or an adsorbent/absorbent agent (e.g., zeolites, activated carbon, etc.).

As used herein, the term "odor" refers to any substance that can stimulate an olfactory response in a human; i.e., sense of smell. As used herein, the term "malodor" and any of its derivative terms refers to an odor that is generally considered unpleasant, obnoxious, or nauseating by the general population, such as the broad spectrum of odors associated with household trash, including odors related to stale urine, feces, vomitus, and putrefying organic materials, e.g., food waste, in common household trash. As used herein, the term "malodor particle" refers to a particle or molecule that carries a malodor. Though it will be understood that a malodor particle includes any particle or molecule that carries a malodor, examples of malodor particles include those derived from sulfide chemistries (e.g., dipropyl trisulfide, propyl mercaptan, dimethyl sulfide, dimethyl trisulfide, methal mercaptan, hydrogen sulfide, etc.), nitrogen chemistries (e.g., trimethylamine, trimethylamine, etc.), or aldehydes, ketones, and/or ester (e.g., demascenone, nonenal, pentanal, methinoal, pentyl acetate, etc.).

As used herein, the terms "lamination," "laminate," and "laminated film," refer to the process and resulting product made by bonding together two or more layers of film or other material. The term "bonding", when used in reference to bonding of multiple layers of a multi-layer film, may be used interchangeably with "lamination" of the layers. According to methods of the present disclosure, adjacent layers of a multi-layer film are laminated or bonded to one another. The bonding purposely results in a relatively weak bond between the layers that has a bond strength that is less than the strength of the weakest layer of the film. This allows the lamination bonds to fail before the film layer, and thus the bond, fails.

The term laminate is also inclusive of coextruded multi-layer films comprising one or more tie layers. As a verb, "laminate" means to affix or adhere (by means of, for example, adhesive bonding, pressure bonding, ultrasonic bonding, corona lamination, and the like) two or more separately made film articles to one another so as to form a multi-layer structure. As a noun, "laminate" means a product produced by the affixing or adhering just described.

As used herein, the terms "partially discontinuous bonding" or "partially discontinuous lamination" refers to lamination of two or more layers where the lamination is substantially continuous in the machine direction or in the transverse direction, but not continuous in the other of the machine direction or the transverse direction. Alternately, partially discontinuous lamination refers to lamination of two or more layers where the lamination is substantially continuous in the width of the article but not continuous in the height of the article, or substantially continuous in the height of the article but not continuous in the width of the article. More particularly, partially discontinuous lamination refers to lamination of two or more layers with repeating bonded patterns broken up by repeating unbounded areas in either the machine direction or the transverse direction.

As used herein, the term "substantially," in reference to a given parameter, property, or condition, means to a degree that one of ordinary skill in the art would understand that the given parameter, property, or condition is met within a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "flexible" refers to materials that are capable of being flexed or bent, especially repeatedly, such that they are pliant and yieldable in response to externally applied forces. Accordingly, "flexible" is substantially opposite in meaning to the terms inflexible, rigid, or unyielding. Materials and structures that are flexible, therefore, may be altered in shape and structure to accommodate external forces and to conform to the shape of objects brought into contact with them without losing their integrity. In accordance with further prior art materials, web materials are provided which exhibit an "elastic-like" behavior in the direction of applied strain without the use of added traditional elastic. As used herein, the term "elastic-like" describes the behavior of web materials which when subjected to an applied strain, the web materials extend in the direction of applied strain, and when the applied strain is released the web materials return, to a degree, to their pre-strained condition.

As used herein, any relational terms such as "first," "second," and "third," "inner," "outer," "upper," "lower," "side," "top," "bottom," etc. are for clarity and convenience in understanding the present disclosure and accompanying drawings and does not connote or depend on any specific preference, orientation, or order, except where the context clearly indicates otherwise. For example, the relational terms may refer an orientation of a multi-layer bag while disposed within a receptacle (e.g., a trash can) for use.

Film Materials

As an initial matter, the thermoplastic material of the films of one or more implementations of the present disclosure may include thermoplastic polyolefins, including polyethylene and copolymers thereof and polypropylene and copolymers thereof. The olefin-based polymers may include ethylene or propylene based polymers such as polyethylene, polypropylene, and copolymers such as ethylene vinyl acetate (EVA), ethylene methyl acrylate (EMA) and ethylene acrylic acid (EAA), or blends of such polyolefins.

Other examples of polymers suitable for use as films in accordance with the present disclosure may include elastomeric polymers. Suitable elastomeric polymers may also be biodegradable or environmentally degradable. Suitable elastomeric polymers for the film include poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), oriented poly(ethylene-terephthalate), poly(ethylene-butylacrylate), polyurethane, poly(ethylene-propylene-diene), ethylene-propylene rubber, nylon, etc.

Some of the examples and description herein below refer to films formed from linear low-density polyethylene. The term "linear low density polyethylene" (LLDPE) as used herein is defined to mean a copolymer of ethylene and a minor amount of an olefin containing 4 to 10 carbon atoms, having a density of from about 0.910 to about 0.926, and a melt index (MI) of from about 0.5 to about 10. For example, some examples herein use an octene comonomer, solution phase LLDPE (MI=1.1; p=0.920). Additionally, other examples use a gas phase LLDPE, which is a hexene gas phase LLDPE formulated with slip/AB (MI=1.0; p=0.920). Still further examples use a gas phase LLDPE, which is a hexene gas phase LLDPE formulated with slip/AB (MI=1.0; p=0.926). One will appreciate that the present disclosure is not limited to LLDPE, and can include "high density polyethylene" (HDPE), "low density polyethylene" (LDPE), and "very low density polyethylene" (VLDPE). Indeed, films made from any of the previously mentioned thermoplastic materials or combinations thereof can be suitable for use with the present disclosure.

Some embodiments of the present disclosure may include any flexible or pliable thermoplastic material that may be formed or drawn into a web or film. Furthermore, each thermoplastic film may include a single layer or multiple layers of thermoplastic materials as described in further detail below in regard to FIGS. 8A-8C. The thermoplastic material may be opaque, transparent, translucent, or tinted. Furthermore, the thermoplastic material may be gas permeable or impermeable.

Additional additives that may be included in one or more embodiments include slip agents, anti-block agents, voiding agents, or tackifiers. Additionally, one or more implementations of the present disclosure include films that are devoid of voiding agents. Some examples of inorganic voiding agents, which may further provide odor control, include the following but are not limited to: calcium carbonate, magnesium carbonate, barium carbonate, calcium sulfate, magnesium sulfate, barium sulfate, calcium oxide, magnesium oxide, titanium oxide, zinc oxide, aluminum hydroxide, magnesium hydroxide, talc, clay, silica, alumina, mica, glass powder, starch, charcoal, zeolites, any combination thereof, etc. Organic voiding agents, polymers that are immiscible in the major polymer matrix, can also be used. For instance, polystyrene can be used as a voiding agent in polyethylene and polypropylene films.

Further additives that may include in one or more embodiments include natural oils. For example, the additives may include thyme oil, mint oil, lemon grass oil, tea tree oil, cinnamon bark oil, methyl jasmonate, etc. Yet further additives may include zinc pyrithione ("ZPT") and copper pyrithione ("CPT"), which inhibit microbial growth.

One of ordinary skill in the art will appreciate in view of the present disclosure that manufacturers may form the films or webs to be used with the present disclosure using a wide variety of techniques. For example, a manufacturer can form a precursor mix of the thermoplastic material and one or more additives. The manufacturer can then form the film(s) from the precursor mix using conventional flat or cast extrusion or coextrusion to produce monolayer, bilayer, or multilayer films. Alternatively, a manufacturer can form the films using suitable processes, such as, a blown film process to produce monolayer, bilayer, or multilayer films. If desired for a given end use, the manufacturer can orient the films by trapped bubble, tenterframe, or other suitable process. Additionally, the manufacturer can optionally anneal the films thereafter.

An optional part of the film-making process is a procedure known as "orientation." The orientation of a polymer is a reference to its molecular organization, i.e., the orientation of molecules relative to each other. Similarly, the process of orientation is the process by which directionality (orientation) is imposed upon the polymeric arrangements in the film. The process of orientation is employed to impart desirable properties to films, including making cast films tougher (higher tensile properties). Depending on whether the film is made by casting as a flat film or by blowing as a tubular film, the orientation process can require different procedures. This is related to the different physical characteristics possessed by films made by the two conventional film-making processes; casting and blowing. Generally, blown films tend to have greater stiffness and toughness. By contrast, cast films usually have the advantages of greater film clarity and uniformity of thickness and flatness, generally permitting use of a wider range of polymers and producing a higher quality film.

When a film has been stretched in a single direction (monoaxial orientation), the resulting film can exhibit strength and stiffness along the direction of stretch, but can be weak in the other direction (i.e., across the stretch), often splitting when flexed or pulled. To overcome this limitation, two-way or biaxial orientation can be employed to more evenly distribute the strength qualities of the film in two directions. Most biaxial orientation processes use apparatus that stretches the film sequentially, first in one direction and then in the other.

In one or more implementations, the films of the present disclosure are blown film, or cast film. Blown film and cast film is formed by extrusion. The extruder used can be a conventional one using a die, which will provide the desired gauge. Some useful extruders are described in U.S. Pat. Nos. 4,814,135; 4,857,600; 5,076,988; 5,153,382; each of which are incorporated herein by reference in their entirety. Examples of various extruders, which can be used in producing the films to be used with the present disclosure, can be a single screw type modified with a blown film die, an air ring, and continuous take off equipment.

In one or more embodiments, a manufacturer can use multiple extruders to supply different melt streams, which a feed block can order into different channels of a multi-channel die. The multiple extruders can allow a manufacturer to form a multi-layer film with layers having different compositions. Such multi-layer film may later be non-continuously laminated with another layer of film.

In a blown film process, the die can be an upright cylinder with a circular opening. Rollers can pull molten plastic upward away from the die. An air-ring can cool the film as the film travels upwards. An air outlet can force compressed air into the center of the extruded circular profile, creating a bubble. The air can expand the extruded circular cross section by a multiple of the die diameter. This ratio is called the "blow-up ratio." When using a blown film process, the manufacturer can collapse the film to double the plies of the film. Alternatively, the manufacturer can cut and fold the film, or cut and leave the film unfolded.

In any event, in one or more embodiments, the extrusion process can orient the polymer chains of the blown film. In particular, the extrusion process can cause the polymer chains of the blown film to be predominantly oriented in the machine direction. The orientation of the polymer chains can result in an increased strength in the direction of the orientation. As used herein predominately oriented in a particular direction means that the polymer chains are more oriented in the particular direction than another direction. One will appreciate, however, that a film that is predominately oriented in a particular direction can still include polymer chains oriented in directions other than the particular direction. Thus, in one or more embodiments the initial or starting films (films before being stretched or bonded or laminated in accordance with the principles described herein) can comprise a blown film that is predominately oriented in the machine direction.

The process of blowing up the tubular stock or bubble can further orient the polymer chains of the blown film. In particular, the blow-up process can cause the polymer chains of the blown film to be bi-axially oriented. Despite being bi-axially oriented, in one or more embodiments the polymer chains of the blown film are predominantly oriented in the machine direction (i.e., oriented more in the machine direction than the transverse direction).

The films of one or more implementations of the present disclosure can have a starting gauge between about 0.1 mils to about 20 mils, suitably from about 0.2 mils to about 4 mils, suitably in the range of about 0.3 mils to about 2 mils, suitably from about 0.6 mils to about 1.25 mils, suitably from about 0.9 mils to about 1.1 mils, suitably from about 0.3 mils to about 0.7 mils, and suitably from about 0.4 mils and about 0.6 mils. Additionally, the starting gauge of films of one or more implementations of the present disclosure may not be uniform. Thus, the starting gauge of films of one or more implementations of the present disclosure may vary along the length and/or width of the film.

As an initial matter, one or more layers of the films described herein can comprise any flexible or pliable material comprising a thermoplastic material and that can be formed or drawn into a web or film. As described above, the film includes a plurality of layers of thermoplastic films. Each individual film layer may itself include a single layer or multiple layers. In other words, the individual layers of the multi-layer film may each themselves comprise a plurality of laminated layers. Such layers may be significantly more tightly bonded together than the bonding provided by the purposely weak discontinuous bonding in the finished multi-layer film. Both tight and relatively weak lamination can be accomplished by joining layers by mechanical pressure, joining layers with adhesives, joining with heat and pressure, spread coating, extrusion coating, and combinations thereof. Adjacent sub-layers of an individual layer may be coextruded. Coextrusion results in tight bonding so that the bond strength is greater than the tear resistance of the resulting laminate (i.e., rather than allowing adjacent layers to be peeled apart through breakage of the lamination bonds, the film will tear).

The following discussion provides more detail with regards to one or more embodiments with reference to the figures. One or more embodiments of the present disclosure include products made from or with thermoplastic films and that include color indicators. For example, such products include, but are not limited to, grocery bags, trash bags, sacks, and packaging materials, feminine hygiene products, baby diapers, adult incontinence products, or other products. For ease in description, however, the figures and bulk of the following disclosure focuses on films and bags. One will further appreciate that the teachings and disclosure equally applies to other products as well. For example, some embodiments of the present disclosure include nonwovens in place of the films described herein. Additional embodiments of the present disclosure include other materials in place of the films described herein.

Referring now to the figures, FIG. 1 is a perspective view of a thermoplastic bag 100 according to an embodiment of the present disclosure. The thermoplastic bag 100 includes a first sidewall 102 and a second sidewall 104. Each of the first and second sidewalls 102, 104 includes a first side edge 106, a second opposite side edge 108, a bottom edge 110 extending between the first and second side edges 106, 108, and a top edge 111 extending between the first and second side edges 106, 108 opposite the bottom edge 110. In some embodiments, the first sidewall 102 and the second sidewall 104 are joined together along the first side edges 106, the second side edges 108, and the bottom edges 110. The first and second sidewalls 102, 104 may be joined along the first and second side edges 106, 108 and bottom edges 110 by any suitable process such as, for example, a heat seal.

In some embodiments, the bottom edge 110 or one or more of the side edges 106, 108 can comprise a fold. In other words, the first and second sidewalls 102, 104 may comprise a single unitary piece of material. The top edges 111 of the first and second sidewalls 102, 104 may define an opening 112 to an interior of the thermoplastic bag 100. In other words, the opening 112 may be oriented opposite the bottom edge 110 of the thermoplastic bag 100. Furthermore, when placed in a trash receptacle, the top edges 111 of the first and second sidewalls 102, 104 may be folded over the rim of the receptacle.

In some embodiments, the thermoplastic bag 100 may optionally include a closure mechanism 114 located adjacent to the top edges 111 for sealing the top of the thermoplastic bag 100 to form an at least substantially fully-enclosed container or vessel. As shown in FIG. 1, in some embodiments, the closure mechanism 114 comprises a draw tape 116, a first hem 120, and a second hem 118. In particular, the first top edge 111 of the first sidewall 102 may be folded back into the interior volume and may be attached to an interior surface of the first sidewall 102 to form the first hem 120. Similarly, the second top edge 111 of the second sidewall 104 is folded back into the interior volume and may be attached to an interior surface of the second sidewall 104 to form a second hem 118. The draw tape 116 extends through the first and second hems 120, 118 along the first and second top edges 111. The first hem 120 includes a first aperture 124 (e.g., notch) extending through the first hem 120 and exposing a portion of the draw tape 116. Similarly, the second hem 118 includes a second aperture 122 extending through the second hem 118 and exposing another portion of the draw tape 116. During use, pulling the draw tape 116 through the first and second apertures 124, 122 will cause the first and second top edges 111 to constrict. As a result, pulling the draw tape 116 through the first and second apertures 124, 122 will cause the opening 112 of the thermoplastic bag 100 to at least partially close or reduce in size. The draw tape closure mechanism 114 may be used with any of the implementations of a thermoplastic bag described herein.

Although the thermoplastic bag 100 is described herein as including a draw tape closure mechanism 114, one of ordinary skill in the art will readily recognize that other closure mechanisms may be implemented into the thermoplastic bag 100. For example, in some embodiments, the closure mechanism 114 may include one or more of flaps or handles, adhesive tapes, a tuck and fold closure, an interlocking closure, a slider closure, a zipper closure, or any other closure structures known to those skilled in the art for closing a bag.

Figure 2B:
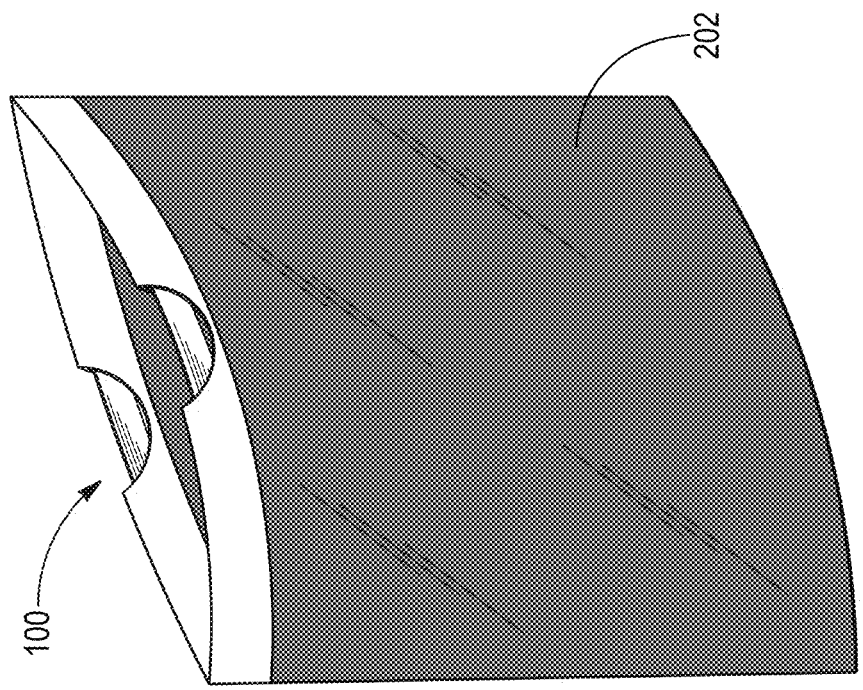
FIGS. 2A-2B illustrate a perspective view of a thermoplastic bag having a color indicator changing a color appearance in accordance with one or more embodiments.
Figure 2A:
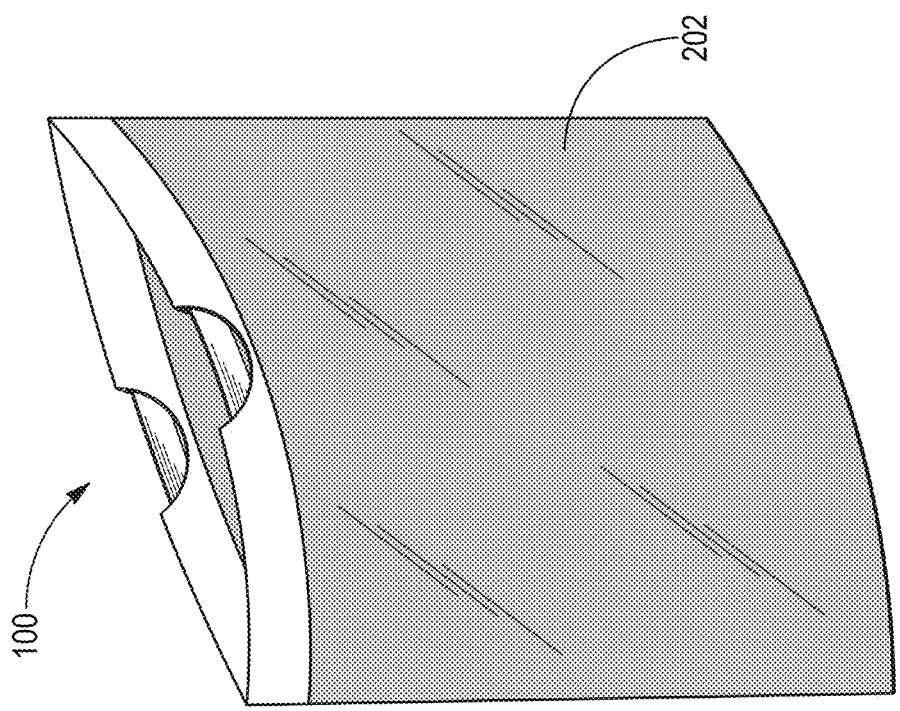

As mentioned above, a color indicator can be applied to thermoplastic films or bags. In particular, the color indicator can be configured to change its color appearance. FIGS. 2A-2B illustrate the thermoplastic bag 100 including a color indicator 202 in accordance with one or more embodiments. Specifically, FIG. 2A illustrates the color indicator 202 having a first color and FIG. 2B illustrates the color indicator 202 having a second color. As shown by FIGS. 2A and 2B, the color indicator 202 can change its color appearance by changing from the first color to the second color (e.g., changing from a green color to a blue color). In one or more embodiments, however, the color indicator 202 can appear as a first color and can change its color appearance by transitioning to a clear appearance. In some embodiments, the color indicator 202 can begin with a clear appearance and transition into a first color. In some embodiments, the color indicator 202 can transition through more than two color appearances (e.g., more than two colors).

Though FIGS. 2A and 2B illustrate the color indicator 202 occupying the entire surface of the thermoplastic bag 100, one or more embodiments apply the color indicator 202 to particular portions of the thermoplastic bag 100 or as particular patterns as will be discussed in more detail with reference to FIGS. 4-7B below.

As mentioned above, the color indicator changes its color appearance in response to a color change trigger. FIGS. 3A-3C illustrate operation of the color indicator in response to a color change trigger in accordance with one or more embodiments. In particular, FIGS. 3A-3C illustrate the color indicator changing its color appearance in response to exposure to malodor particles.

FIG. 3A illustrates the thermoplastic bag 100 including a color indicator 302 and positioned within a trash receptacle 304. As shown in FIG. 3A, the color indicator 302 has a first color. Further, as shown, there are no malodor sources (e.g., articles of trash) within the thermoplastic bag 100. Accordingly, the color indicator 302 maintains the first color to indicate that there are no malodors (i.e., malodor particles) present within the thermoplastic bag 100.

FIG. 3B shows another embodiment of the thermoplastic bag 100 including the color indicator 302 and positioned within the trash receptacle 304. In particular, FIG. 3B illustrates the thermoplastic bag 100 after a set of malodor sources 306 have been added. As shown, the set of malodor sources 306 produces malodor particles 308.

As shown in FIG. 3B, in response to the presence of the malodor particles 308, the color indicator 302 begins to transition from the first color to a second color. In one or embodiments, the color indicator 302 transitions completely to the second color in the presence of the malodor particles 308 (i.e., as soon as any malodor particles are present within the thermoplastic bag 100). In some embodiments, as shown in FIG. 3B, the color indicator 302 only transitions partially to the second color. In other words, the color indicator 302 can be configured to complete the transition from the first color to the second color only when a significant amount of malodor particles (e.g., an amount exceeding some threshold) are present within the thermoplastic bag 100. Such embodiments provide an advantageous controlled release that avoids transitioning to the second color too early, and thus avoids causing a user to replace the thermoplastic bag 100 prematurely. In some embodiments, the color indicator 302 is configured to transition to an intermediate color in the presence of the malodor particles 308 but before there is a significant amount of malodor particles.

FIG. 3C illustrates another embodiment of the thermoplastic bag 100 including the color indicator 302 and positioned within the trash receptacle 304. In particular, FIG. 3C illustrates the thermoplastic bag 100 after additional malodor sources have been added to the set of malodor sources 306. As shown, because the set of malodor sources 306 now includes additional malodor sources, the set of malodor sources 306 produces additional malodor particles to add to the malodor particles 308. In response, the color indicator 302 transitions completely to the second color. This ideally enables the thermoplastic bag 100 to provide a visual indication of the presence of malodors resulting from the trash that is added over a period of time. Further, as the color indicator 302 progresses through the transition to the second color, the color indicator 302 provides a visual indication of the quantity or strength of malodors present within the thermoplastic bag 100.

In one or more embodiments, the color indicator 302 is configured to change its appearance based on the chemical structure of the malodor particles 308. In particular, some embodiments involve configuring the color indicator to change its color appearance based on a chemical structure that provides the malodor particles 308 with a particular pH level. For example, the color indicator 302 can be configured to change its color appearance only when exposed to malodor particles having a specific pH level (e.g., 6.5) or a pH level within a range of predetermined pH levels (e.g., 5.0-6.5 inclusive). Malodor particles having a pH level that falls out of the specific pH level or the range of predetermined pH levels, respectively, would not induce a change of color appearance. Even though FIGS. 3A-3C specifically illustrate a response to exposure to malodor particles, in one or more embodiments, the color indicator 302 can change its color appearance in response to exposure to other particles having a chemical structure that provides the particles with a particular pH level. Some examples of such pH-driven color indicators include methyl violet, thymol blue, methyl orange, bromocresol green, methyl red, litmus, bromothymol blue, phenol red, phenolphthalein, thymolphthalein, alizarin yellow R, and anthocyanin.

Because the color indicator 302 can be configured to change its color appearance in response to exposure to malodor particles, the color indicator 302 can be configured to change its color appearance without contacting the malodor sources. For example, a malodor source may be positioned within the center of the thermoplastic bag so that it does not touch the first and second sidewalls 102, 104 or the bottom edge 110 of the thermoplastic bag 100. However, the malodor source can produce malodor particles that can move around within the thermoplastic bag 100. Through exposure to these malodor particles, the color indicator 302 can change its color appearance. Thus, the color indicator 302 can operate effectively even when there is no contact with a malodor source.

As mentioned, the color indicator 302 can additionally or alternatively be configured to change its color appearance in response to other color change triggers. For example, in one or more embodiments, the color indicator 302 is configured to change its color appearance based on exposure to moisture or moisture absorption. In particular, as malodor sources are added to the thermoplastic bag 100, any moisture provided by the malodor sources (e.g., moisture vapor resulting from evaporation) can trigger the color indicator 302 to change colors. As a non-limiting example, a moisture-driven color indicator can include general transition metal complexes (e.g., cobalt chloride).

In further embodiments, the color indicator 302 can change its color appearance as a result of oxidation. As an example, magnesium dioxide (a yellow/brown color) can produce a manganite ion (a green color) through oxidation, which can produce a permanganate ion (a purple color) through further oxidation. As another example, methylene blue turns a blue color when oxidized but becomes clear when reduced. To illustrate, in one or more embodiments, the color indicator 302 is configured to provide an aesthetically pleasing visual. Consequently, the color indicator 302 can be configured to change its color appearance based on exposure to the surrounding air.

Figure 4:
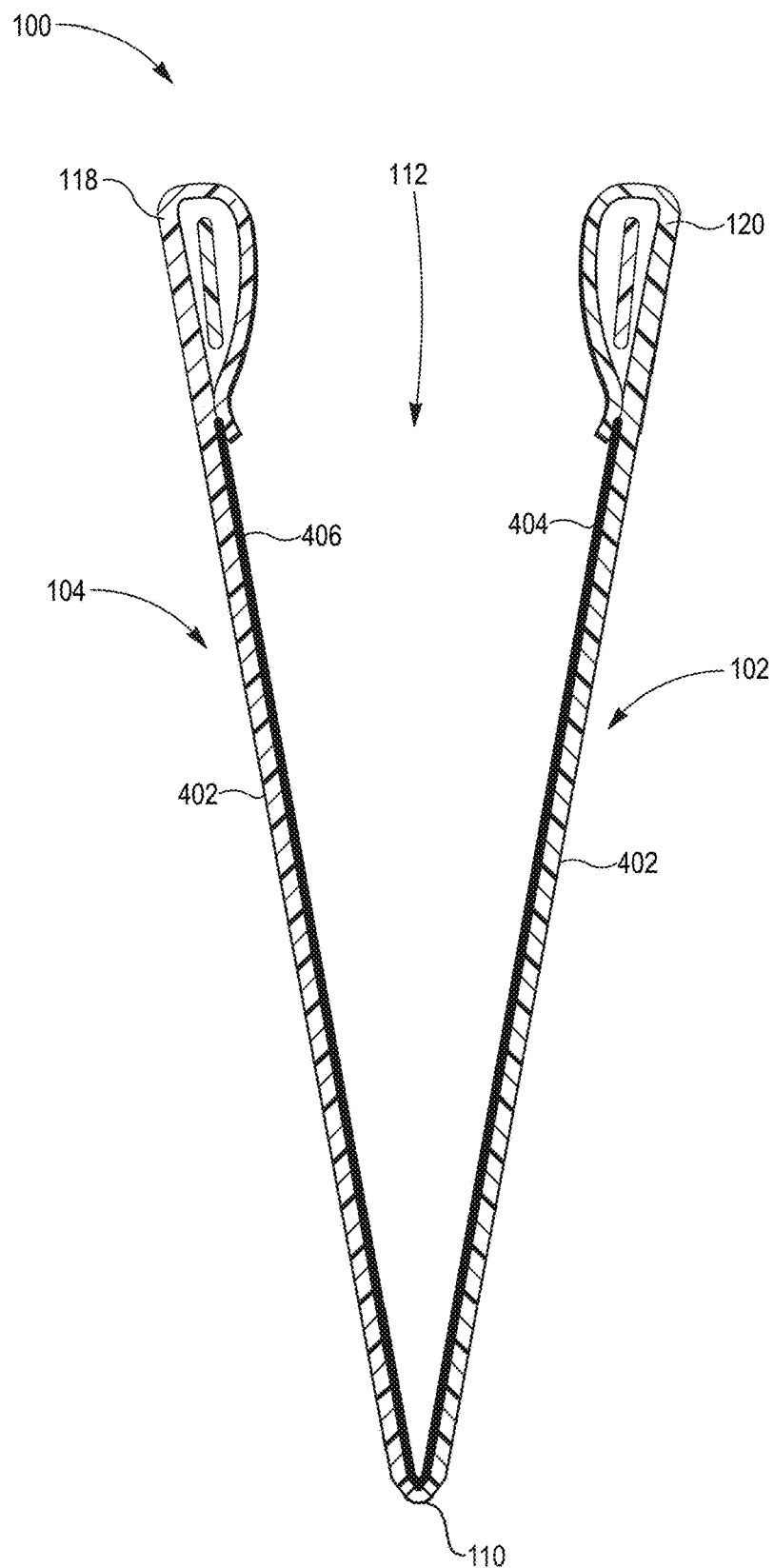
FIG. 4 illustrates a side cross-sectional view of another thermoplastic bag having a color indicator in accordance with one or more embodiments.

As mentioned above, the color indicator can be disposed onto the thermoplastic bag 100 in a variety of ways. FIG. 4 illustrates a side cross-sectional view of the thermoplastic bag 100 of FIG. 1 having the color indicator disposed thereon in accordance with one or more embodiments. As shown in FIG. 4, each of the first sidewall 102 and the second sidewall 104 of the thermoplastic bag 100 includes a single layer of thermoplastic film 402. The thermoplastic film 402 of the first sidewall 102 and the second sidewall 104 can include any of the thermoplastic films described above. In one or more embodiments, each of the first and second sidewalls 102, 104 of the thermoplastic bag 100 includes multiple layers of thermoplastic film as will be discussed in more detail with reference to FIGS. 7A-7B.

Additionally, as shown in FIG. 4, the thermoplastic bag includes the color indicator 404 disposed to cover an interior surface of the first sidewall 102 (i.e., the surface of the sidewall facing the opening 112 of the thermoplastic bag 100) and the color indicator 406 disposed to cover an interior surface of the second sidewall 104. In one or more embodiments, however the color indicators 404, 406 are disposed on an exterior surface of the respective sidewall. Further, some embodiments involve coextruding the color indicator 404 with the first sidewall 102 and the color indicator 406 with the second sidewall 104 (i.e., embedding the color indicators 404, 406 as an additive into the thermoplastic film forming the first sidewall 102 and the second sidewall 104, respectively, during the extrusion process) as discussed above. By disposing the color indicators 404, 406 to cover the entire available surface, the thermoplastic bag 100 supplies a greater amount of the color indicator, providing a more visible (i.e., more prominent) indication of the presence of malodors.

In one or more embodiments, the thermoplastic bag 100 only includes one color indicator (i.e., the color indicators 404, 406 include the same color indicator). In some embodiments, however, the thermoplastic bag 100 includes multiple color indicators. For example, the color indicators 404, 406 can each include a different color indicator (e.g., a color indicator configured to change its color appearance in response to a different set of malodor particles). To illustrate, the color indicator 404 can be configured to change its color appearance when exposed to a first set of malodor particles, and the color indicator 406 can be configured to change its color appearance when exposed to a second set of malodor particles. More specifically, the color indicator 404 can be configured to change its color appearance when exposed to malodor particles having a first chemical structure giving the malodor particles a first pH value (or a pH value within a first range of pH values) and the color indicator 406 can be configured to change its color appearance when exposed to malodor particles having a second chemical structure giving the malodor particles a second pH value (or a pH value within a second range of pH values). In this way, the thermoplastic bag 100 can provide a visual indication regarding the type or potency of malodors present.

Figure 5:
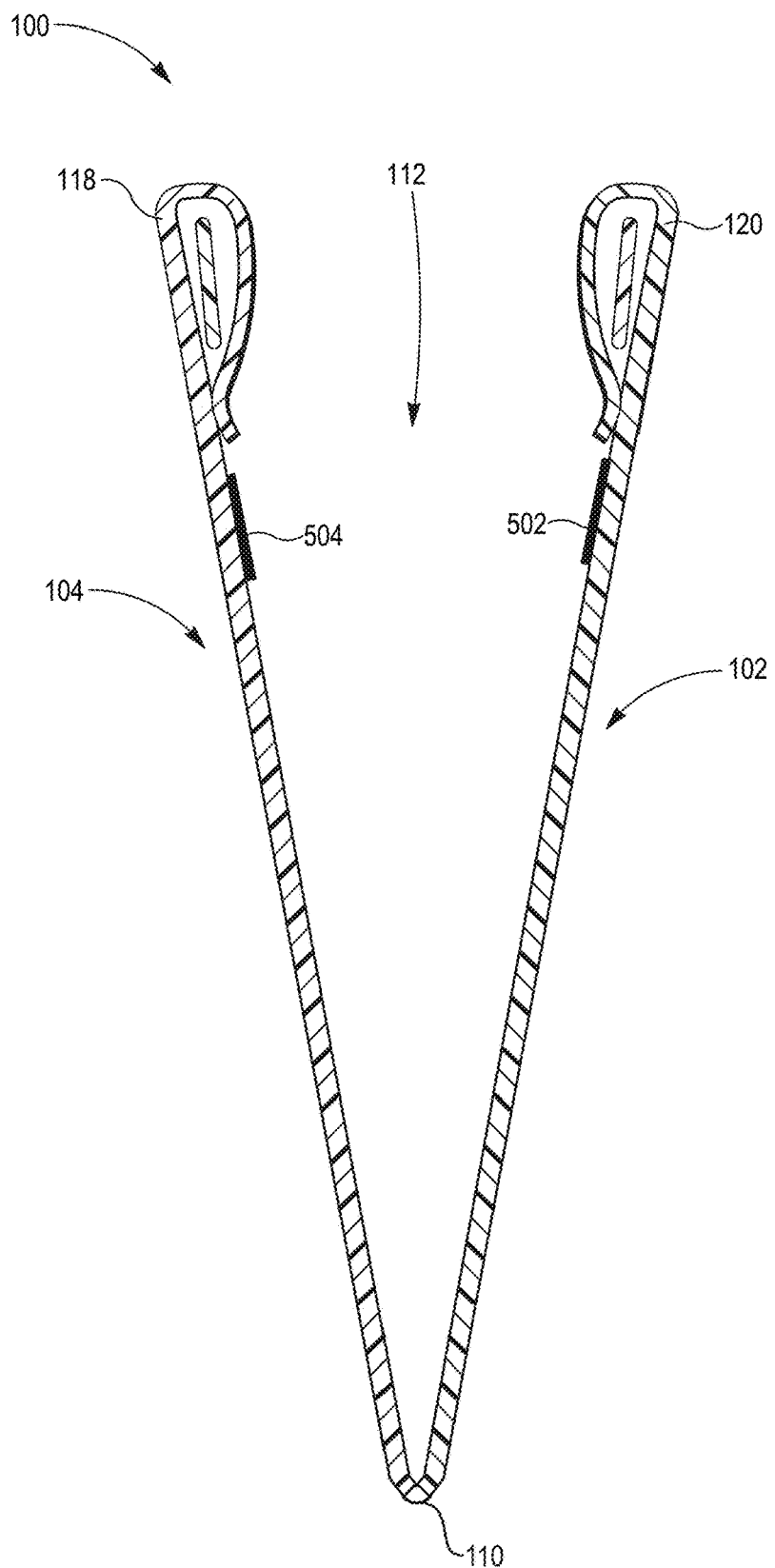
FIG. 5 illustrates a side cross-sectional view of yet another thermoplastic bag having a color indicator in accordance with one or more embodiments.

FIG. 5 illustrates another side cross-sectional view of the thermoplastic bag 100 of FIG. 1 having the color indicator disposed thereon in accordance with one or more embodiments. As shown in FIG. 5, the thermoplastic bag 100 includes the color indicator disposed as a first strip 502 and a second strip 504 onto the first sidewall 102 and the second sidewall 104, respectively. In one or more embodiments, the first strip 502 and the second strip 504 include the same color indicator. In some embodiments, the first strip 502 and the second strip 504 include different color indicators as discussed with reference to FIG. 4. Though FIG. 5 illustrates the first strip 502 and the second strip 504 positioned near the top of the respective sidewall, in one or more embodiments, the strips can be positioned lower. Further, while FIG. 5 illustrates the color indicator in the form of a strip, in other embodiments, the color indicator can be applied to the thermoplastic bag 100 in other patterns. For example, the color indicator can be applied as a series of dots, one or more streaks, or some other preestablished or arbitrary pattern. As shown in FIG. 5, positioning the color indicator near the hem (e.g., the top of the bag 100) can help ensure that a user will be able to view the color indicator, even when the bag 100 is full of waste or positioned within a trash receptacle.

Figure 6:
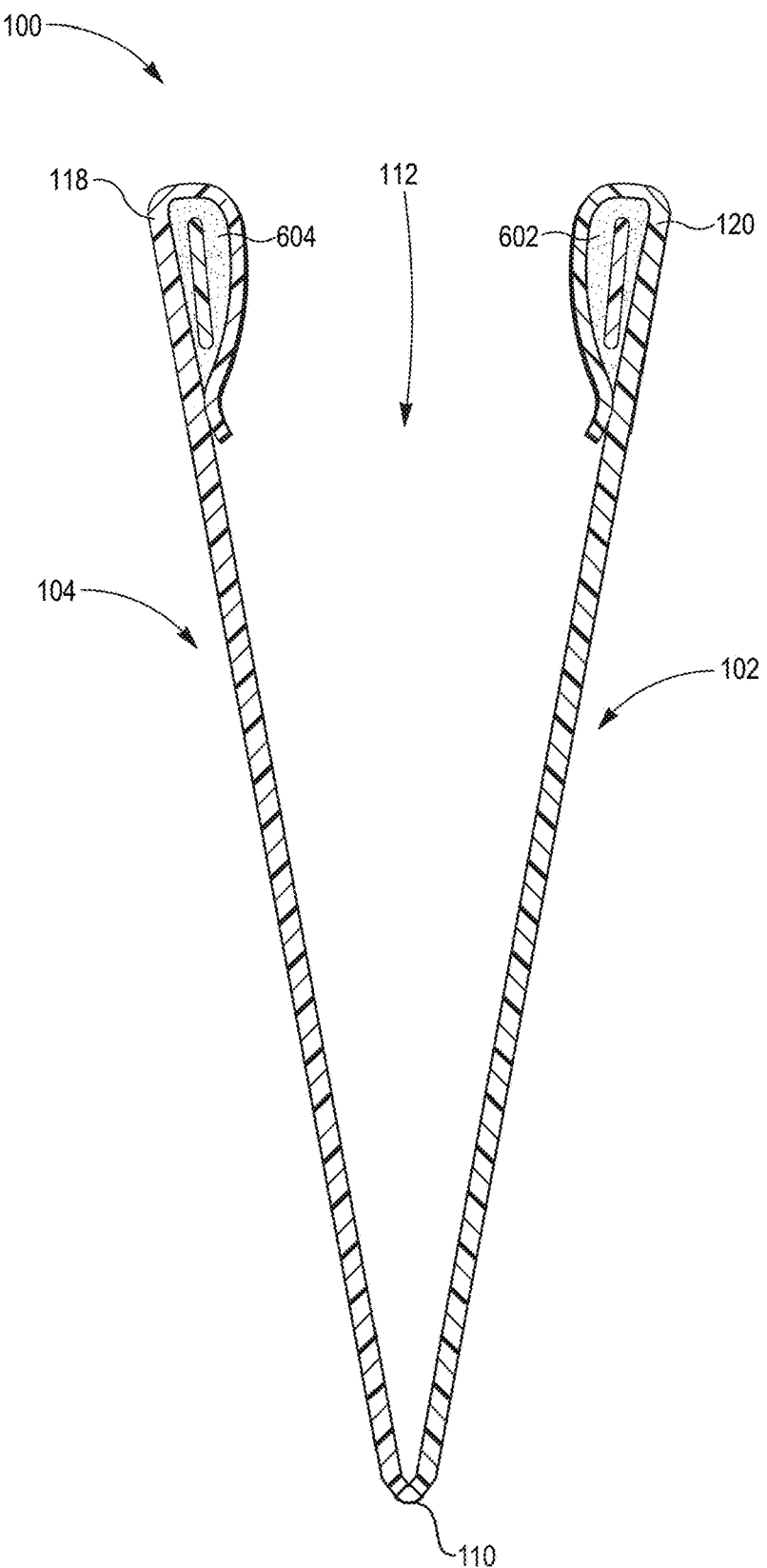
FIG. 6 illustrates a side cross-sectional view of yet another thermoplastic bag having a color indicator in accordance with one or more embodiments.

FIG. 6 illustrates another side cross-sectional view of the thermoplastic bag 100 of FIG. 1 having the color indicator disposed thereon in accordance with one or more embodiments. As shown in FIG. 6, the thermoplastic bag 100 includes the color indicator 602 disposed within the first hem 120 and the color indicator 604 disposed within the second hem 118 of the thermoplastic bag 100. In one or more embodiments, the color indicators 602, 604 include the same color indicator. In some embodiments, the color indicators 602, 604 include different color indicators as discussed with reference to FIG. 4. By disposing the color indicator within the hems, the thermoplastic bag 100 can include color indicator applications that are not consumer friendly (e.g., not visually attractive, sticky, oily, powder, etc.) as will be discussed in more detail with regards to FIGS. 7A-7B. In particular, positioning the color indicator within the hem can help ensure that a user does not come into direct contact with the color indicator.

Figures 7A, 7B:
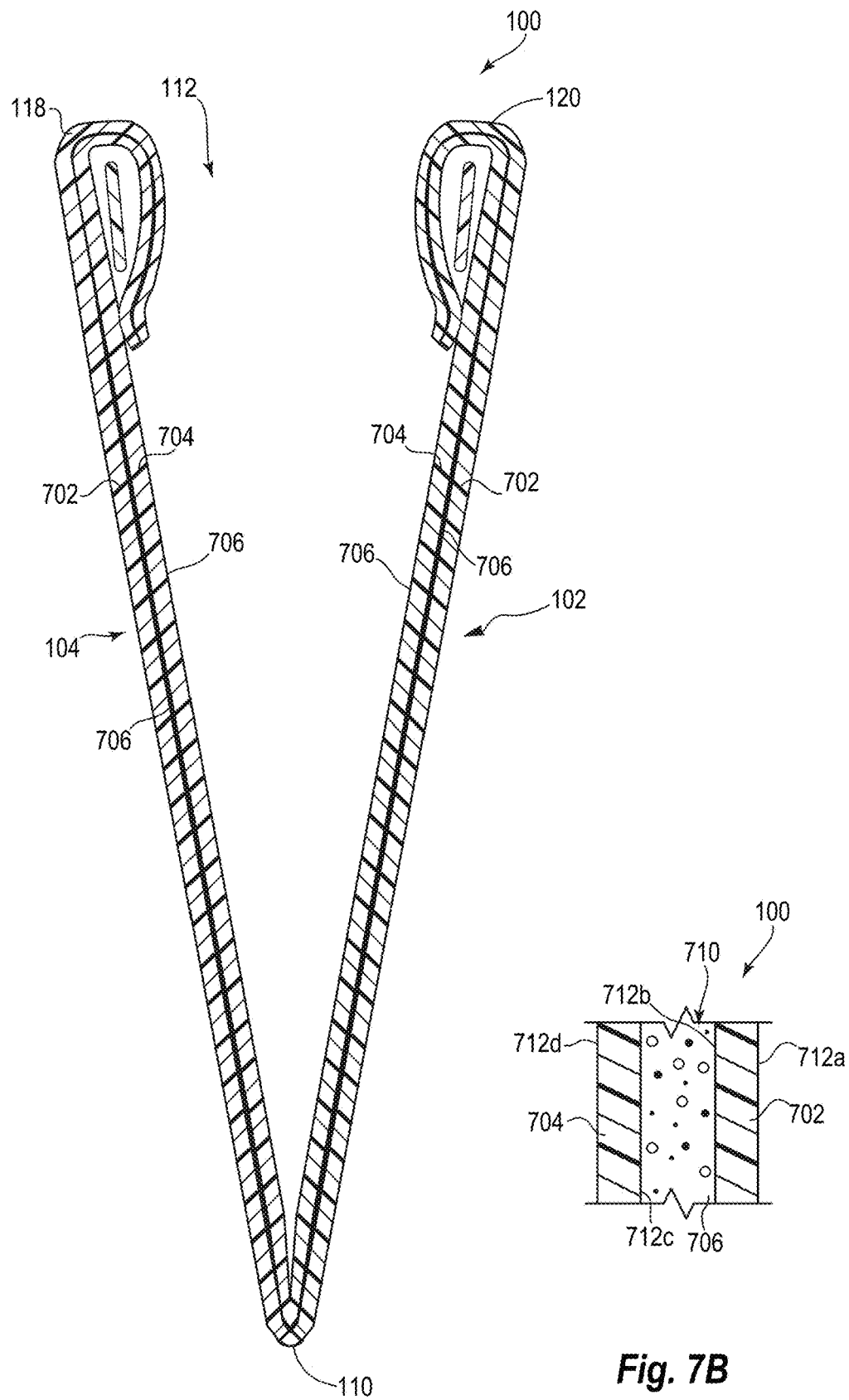
FIG. 7A illustrates a side cross-sectional view of yet another thermoplastic bag having a color indicator in accordance with one or more embodiments.
FIG. 7B shows an enlarged partial side cross-sectional view of a sidewall of the thermoplastic bag of FIG. 7A.

FIG. 7A is a side cross-sectional view of the thermoplastic bag 100 of FIG. 1. FIG. 7B is an enlarged view of the side cross-sectional view of the thermoplastic bag 100 of FIG. 7A. Referring to FIGS. 7A and 7B together, each of the first and second sidewalls 102, 104 of the thermoplastic bag 100 includes multiple layers of thermoplastic film. In particular, each of the first and second sidewalls 102, 104 includes a first film 702 and a second film 704. The thermoplastic bag 100 further comprises a color indicator 706 disposed on one or more of the first and second films 702, 704. When disposed within a receptacle (e.g., trash can), the first film 702 of each of the first and second sidewalls 102, 104 (referred to herein collectively as "the first film 702") of the thermoplastic bag 100 may face (e.g., be oriented adjacent and proximate to) the receptacle, and the second film 704 of each of the first and second sidewalls 102, 104 (referred to herein collectively as "the second film 704") may face (e.g., at least partially define) the interior of the of the thermoplastic bag 100.

The first and second films 702, 704 may include films such as any of the films described above. As mentioned briefly above, the color indicator 706 may be disposed on one or more of the first film 702 and the second film 704. Specifically, the first and second films 702, 704 may be at least partially dosed with the color indicator 706. In some embodiments, the color indicator 706 is disposed between the first and second films 702, 704. As used herein, the term "between," when referring to the color indicator 706 and the first and second films 702, 704, means that the color indicator 706 is disposed at least partially within a space separating at least a portion of the first film 702 and at least a portion of the second film 704. Thus, the color indicator 706 can be disposed on one or more of the first and second films 702, 704 (e.g., on a side of the first and second films 702, 704 facing the space separating the first and second films 702, 704 from each other). Furthermore, the color indicator 706 can be disposed at least partially in (e.g., at least partially embedded in) one or more of the first and second films 702, 704.

In some embodiments, the color indicator 706 can at least substantially fully span an area between the first film 702 and the second film 704. In other words, the color indicator 706 can at least substantially fully span a length and width of the first and second films 702, 704. In other embodiments, the color indicator 706 may be disposed between only portions of the first and second films 702, 704. In other words, the color indicator 706 may not be continuous and may span only portions of the area between the first film 702 and the second film 704. In additional embodiments, the color indicator 706 is included in the first and second films 702, 704 (via inclusion in master batch used to form the first and second films 702, 704) in addition to being disposed between the first and second films 702, 704.

In some embodiments, the first and second sidewalls 102, 104 include an air gap 710 between the first and second films 702, 704 that works in conjunction with the color indicator 706. In one or more embodiments, the air gap 710 provides a means of trapping malodor. For example, malodor can pass into the air gap 710 and be at least partially trapped within the air gap 710. Thus, the air gap 710 can reduce or prevent malodor from passing through the outer film (i.e., the first film 702) of the thermoplastic bag 100. Additionally, one or more embodiments include the color indicator 706 within the air gap 710 that can operate to change its color appearance. Having the color indicator 706 within the air gap 710 can influence the change rate or allow for a delay in color change as the malodor particles (or moisture or oxidizing agents) would have to first penetrate the inner film (i.e., the second film 704). Furthermore, one or more embodiments involve using the air gap 710 to alter the pH of odoriferous species and mitigate formation of odor causing agents.

The air gap 710 can provide an area for disposition of the color indicator 706 that conceals the color indicator 706. Thus, one or more embodiments includes a color indicator that is unsuitable for use in an unconcealed portion of a bag. For example, the color indicator 706 between the first and second films 702, 704 can comprise a color indicator 706 that lacks aesthetically pleasing characteristics generally desired by consumers. In another embodiment, the color indicator 706 comprises negative effects to a consumer, such as skin irritation issues, dust inhalation issues, or other negative effects when combined with consumer interaction. In another embodiment, the color indicator 706 is disposed in a wet (i.e., liquid) application that can have a negative effect for users of the bag. The air gap 710 can prevent a user from touching or accessing such wet color indicators.

Additionally, the ability to place color indicators in between layers is helpful in preserving longevity and synergy. In particular, the capability to place a color indicator between films can avoid color appearance changes before malodor sources have been discarded in the thermoplastic bag 100. Along similar lines, the ability to place a color indicator in the air gap between the first and second films 702, 704 can facilitate higher levels of color indicator dosing without exposing a user to an oily (or other undesirable) feel inside the bag.

Furthermore, in some embodiments, the location where the color indicator 706 is disposed between the first film 702 and the second film 704 may be selected based on where the malodor particles will be located relative to the thermoplastic bag 100. For example, the color indicator 706 may be disposed between the first film 702 and the second film 704 at the bottom area of the thermoplastic bag 100 (e.g., a portion of the bag most likely to be exposed to malodor molecules). Furthermore, in some embodiments, the one or more substances of the color indicator 706 may be selected based on where the color indicator 706 will be located relative to the thermoplastic bag 100.

As shown in FIGS. 7A and 7B, the inner surface 712d of the thermoplastic bag 100 can have a first surface area. In some embodiments, the inner surface 712d is the only surface upon which color indicators are applied. One will appreciate in light of the disclosure herein that the thermoplastic bag 100 includes additional surfaces 712b and 712c (i.e., the surfaces of the first and second films 702, 704 facing each other and forming the air gap 710). Thus, in one or more embodiments, the thermoplastic bag 100 can have the color indicator 706 applied to a total surface area that is greater than the surface area of the inside layer of the thermoplastic bag 100 (i.e., by applying the color indicator 706 to surfaces 712a, 712b, and/or 712c).

In one or more embodiments, the color indicator 706 may comprise a bonding layer. In other words, the color indicator 706 may at least partially bond the first film 702 to the second film 704. For example, the color indicator 706 may include one or more of an adhesive, glue, tackifier, tapes, or any other known material for bonding films together.

Figure 8C:
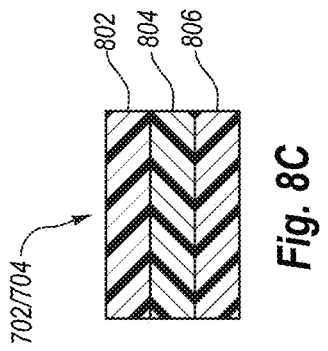
FIGS. 8A-8C show partial side cross-sectional views of films having varying numbers of layers.
Figure 8B:
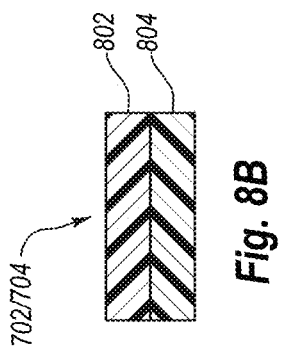
Figure 8A:
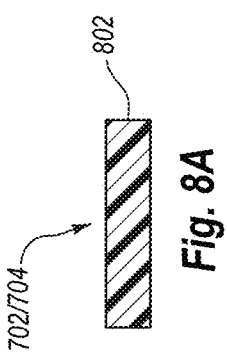

FIGS. 8A-8C are partial cross-sectional views of films that may be used herein as the first and second films 702, 704 of FIGS. 7A-7B. Referring to FIGS. 7A-8C together, in some embodiments, one or more of the first and second films 702, 704 may include a single first layer 802, as shown in FIG. 8A. In other embodiments, one or more of the first and second films 702, 704 may include two layers (i.e., a bi-layer film), as shown in FIG. 8B. For example, the first film 702 may include a first layer 802 and a second layer 804. In such embodiments, the first and second layers 802, 804 may optionally include different grades of thermoplastic material and/or include different additives, including polymer additives. In yet other embodiments, one or more of the first and second films 702, 704 may include three layers 802, 804, 806 (i.e., a tri-layer film), as shown in FIG. 8C. For example, the first film 702 may include a first layer 802, a second layer 804, and a third layer 806. In yet other embodiments, one or more of the first and second films 702, 704 may include more than three layers. In one or more embodiments, the layers of the first and second films 702, 704 are coextruded.

Figure 9B:
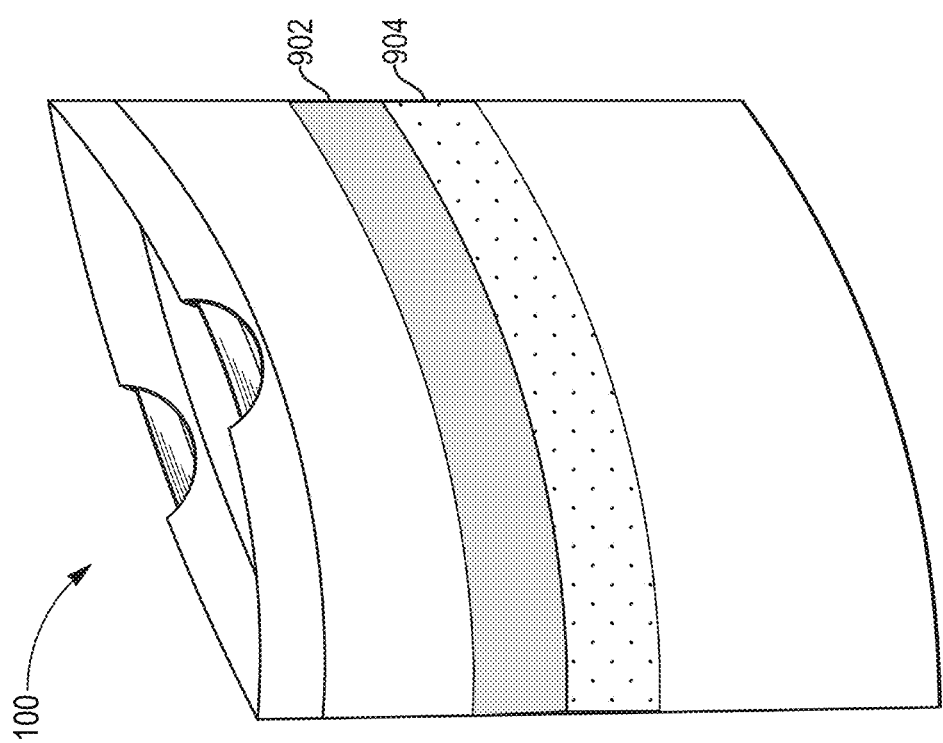
FIGS. 9A-9B illustrate a perspective view of a thermoplastic bag having an odor control component and a color indicator in accordance with one or more embodiments.
Figure 9A:
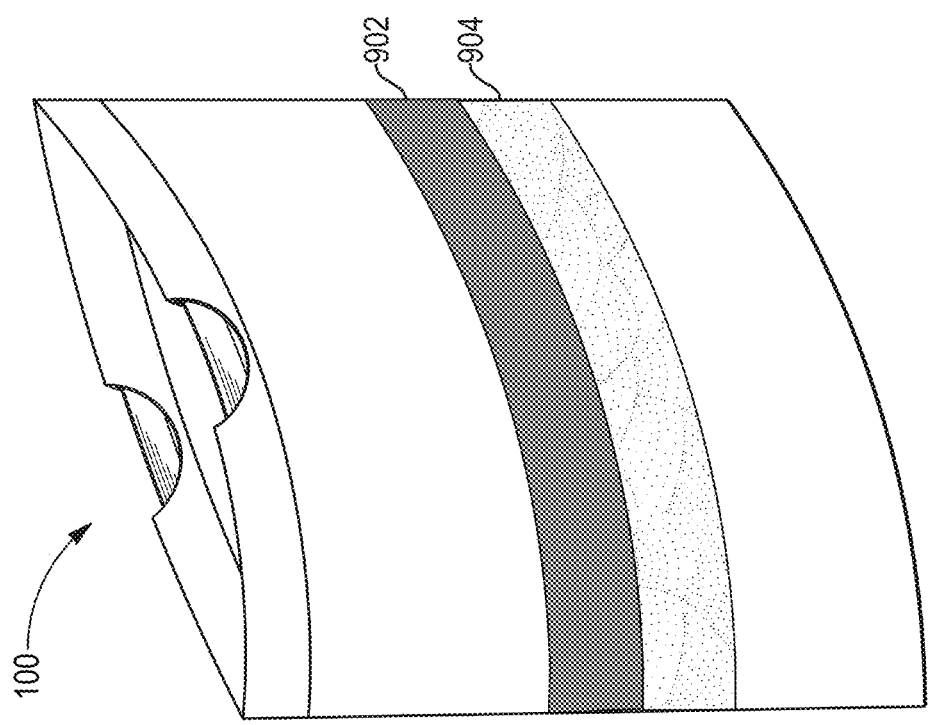

As mentioned above, in one or more embodiments, the thermoplastic bag 100 further includes an odor control component configured to mask, neutralize, or otherwise control malodors produced by malodors sources within the thermoplastic bag 100. Consequently, the color indicator can be configured to change its color appearance to indicate performance of the odor control component. FIGS. 9A-9B illustrate the thermoplastic bag 100 including an odor control component in accordance with one or more embodiments. In particular, FIG. 9A illustrates the color indicator 902 having a first color and a large quantity of the odor control component 904. Although FIG. 9A illustrates the color indicator 902 positioned adjacent to the odor control component 904, it will be appreciated that the color indicator 902 and the odor control component 904 can be positioned anywhere on the thermoplastic bag 100—including in the same location (e.g., layered on top of one another)—without losing efficacy.

As the odor control component 904 operates to mask, neutralize, or otherwise control malodors, the color indicator 902 simultaneously changes from a first color to a second color to indicate performance of the odor control component 904. For example, in one or more embodiments, the odor control component 904 comprises an encapsulated odor control component containing an odor control active in an encapsulant. The encapsulated odor control component can be configured to release the odor control active from the encapsulant when exposed to malodor particles. As the encapsulated odor control component releases the odor control active from the encapsulant, the color indicator 902 simultaneously changes its color appearance.

As discussed above with reference to FIGS. 3A-3C, in one or more embodiments, the color indicator 902 can change its color appearance based on exposure to the malodor particles. In some embodiments, the color indicator can change its color appearance based on exposure any moisture provided by the malodor sources. Further embodiments involve the color indicator 902 changing its color appearance as a result of oxidation.

In one or more embodiments, the color indicator 902 slowly fades in color as the odor control component 904 operates to mask, neutralize, or otherwise control malodors. For example, where the odor control component 904 encapsulates an odor control active, the color indicator 902 can change its color appearance as the odor control component 904 releases odor control active from the encapsulant. To illustrate, in some embodiments, the color indicator 902 includes a chromophore having chemical bonds that oxidize as the odor control active is released. The oxidation can shift the absorption of the chromophore outside the visible light spectrum. Alternatively, the oxidation can remove the chromophore's ability to absorb light and emit a color altogether.

In some embodiments, the color indicator 902 changes its color appearance based on exposure to the odor control active itself. To illustrate, where the odor control component 904 encapsulates an odor control active, exposure to the odor control active as it is released from the encapsulant causes the color indicator 902 to change its color. In particular, the odor control active can have a pH level that causes the color indicator 902 to change its color appearance. Consequently, the color indicator 902 can change colors more quickly when exposed to both malodor particles and the odor control active having a pH value that would induce a change in color appearance. In other words, the rate of change of the color appearance can be based, at least in part, on a chemistry of the odor control component 904 (i.e., the pH level of the odor control active). This advantageously enables better control over the rate of change of the color change appearance. In particular, the odor-control active can be selected, or otherwise designed, based on the rate at which it will induce a color change. Additionally, or alternatively, the rate of change of the color appearance can be based, at least in part, on the concentration of the odor control component 904.

FIG. 9B illustrates the thermoplastic bag 100 from FIG. 9A after most of the odor control component 904 has been depleted (e.g., most of the encapsulated odor control active has been released) and the color indicator 902 has changed to a second color indicating the performance of the odor-control component. For example, by changing its color appearance, the color indicator 902 shows that the odor control component 904 is controlling malodors within the thermoplastic bag 100. Further, by changing its color appearance, the color indicator 902 provides an indication of how much supply of the odor control component 904 remains. In particular, as the color indicator 902 progresses through its transition to the second color, the color indicator shows that there is less of the odor control component 904 remaining to control malodors added to the thermoplastic bag 100 in the future. Though FIG. 9B illustrates that the color indicator 902 has changed from a first color to a second color to indicate performance of the odor control component 904, one or more embodiments involve the color indicator 902 beginning as clear and transitioning to a first color, or beginning as a first color and becoming clear, as discussed above.

Because the color indicator can be disposed in a variety of ways, the color indicator can be effective even when applied to variations of the thermoplastic bag 100. For example, the encapsulated odor control component can be used with patterned variations of the thermoplastic bag 100.

Figure 10:
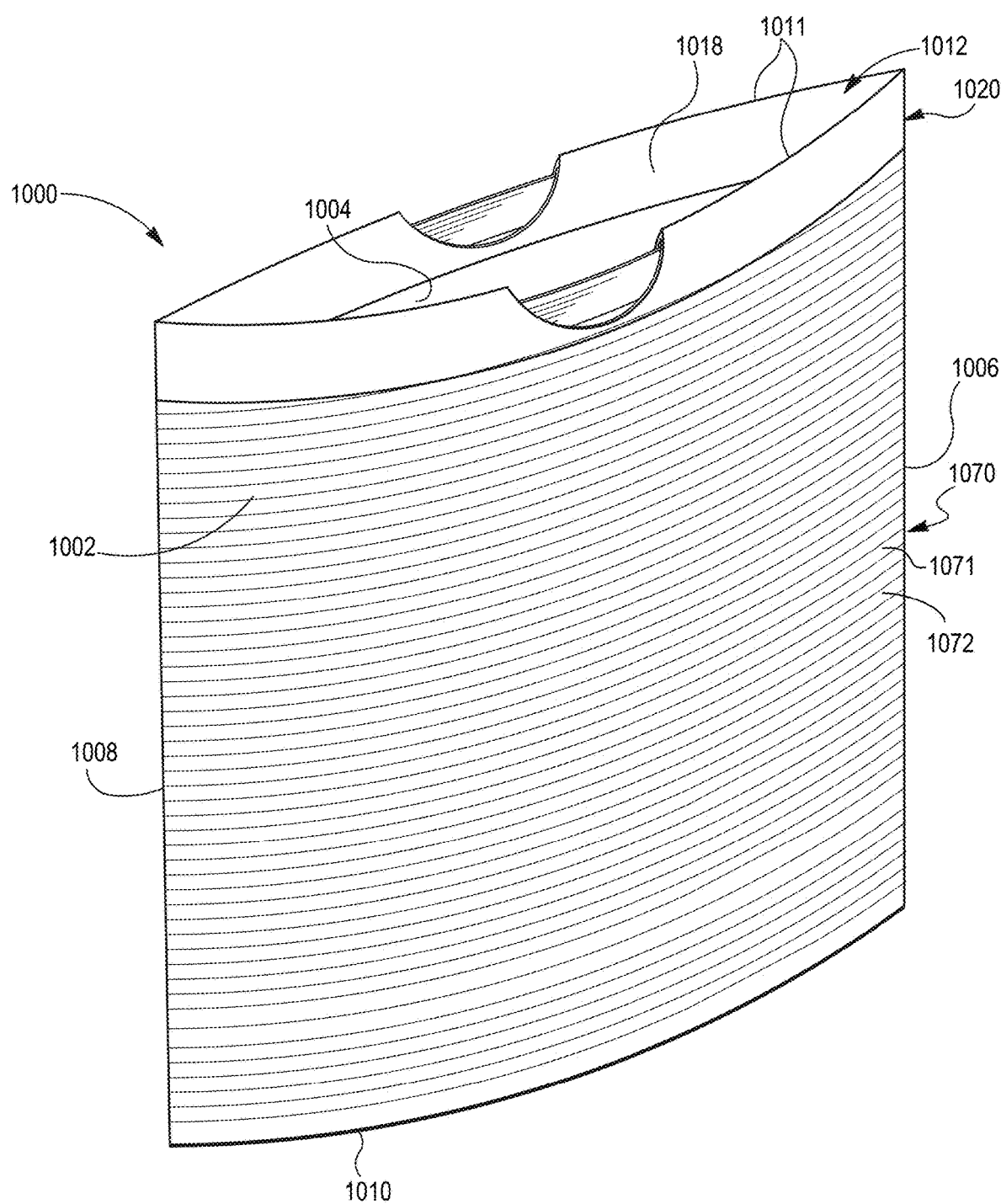
FIG. 10 illustrates a perspective view of a thermoplastic bag having a pattern in accordance with one or more embodiments.

For example, FIG. 10 illustrates a thermoplastic bag 1000 similar to the thermoplastic bag 100, albeit that the sidewalls 1002, 1004 are incrementally stretched. In particular, the sidewalls 1002, 1004 include a ribbed pattern 1070 of a plurality of alternating thinner (e.g., stretched) linear webs 1071 and thicker linear ribs 1072 that may extend across the sidewalls 1002, 1004 between the first side edge 1006 and second side edge 1008. As illustrated in FIG. 10, the webs 1071 and ribs 1072 may be parallel and adjacent to one another. Additionally, as illustrated in FIG. 10, the ribbed pattern 1070 may extend from the bottom edge 1010 toward the opening 1012. To avoid interfering with the operation of the draw tape, the extension of the ribbed pattern 1070 may terminate below the hems 1018, 1020. In alternative implementations, the ribbed pattern 1070 can extend from the bottom edge 1010 to the top edge 1011 of each sidewall. The ribbed pattern 1070 can be formed by passing the films of the sidewalls 1002, 1004 through a pair of transverse direction intermeshing ring rollers, such as those described in U.S. Pat. No. 9,669,595, the contents of which are hereby incorporated herein by reference in their entirety.

Figure 11:
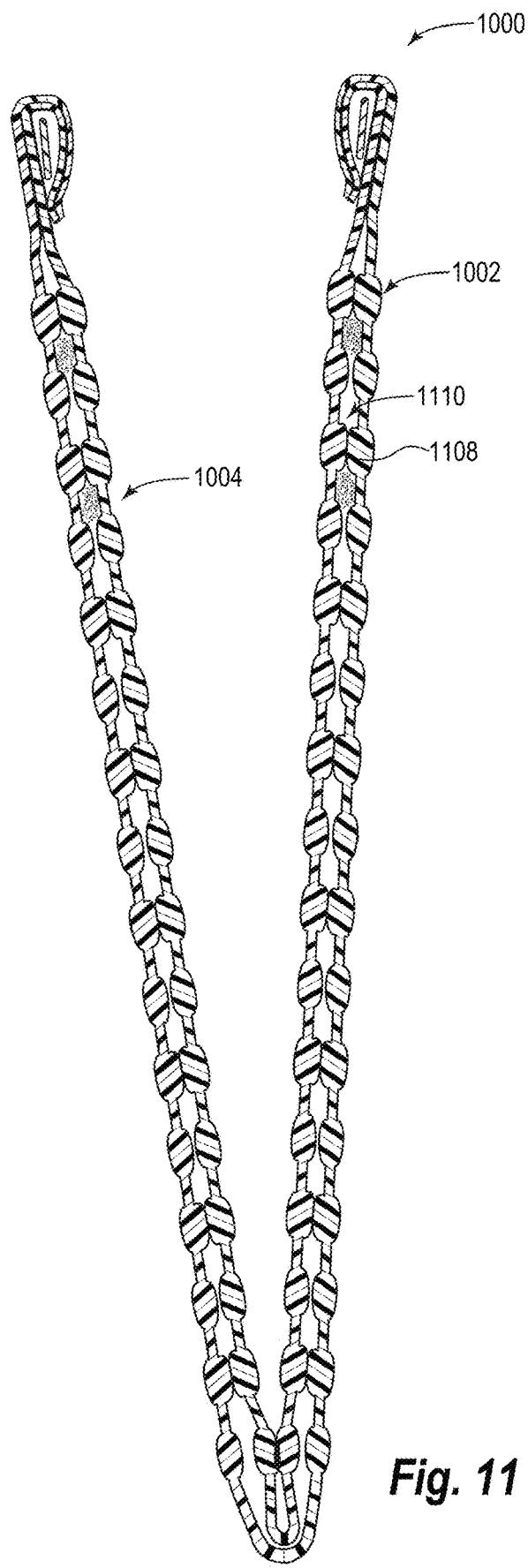
FIG. 11 illustrates a side cross-sectional view of the thermoplastic bag of FIG. 10.

FIG. 11 illustrates a side cross-sectional view of the thermoplastic bag 1000 of FIG. 10. In particular, FIG. 11 shows the thermoplastic bag 1000 wherein each of the sidewalls include multiple layers. As shown in FIG. 11, the multi-layer sidewalls of the thermoplastic bag 1000 include bonded regions 1108 and un-bonded regions or air gaps 1110. In one or more embodiments, the un-bonded regions or air gaps 1110 are located at each sidewall where the sidewall has been stretched or cold-formed (i.e., at the location of the stretched linear webs 1071 discussed with reference to FIG. 10). In some embodiments, the un-bonded regions or air gaps 1110 are located at each sidewall where the sidewall has not been stretched or cold-formed (i.e., at the location of the linear ribs 1072 of FIG. 10). In some embodiments, the bonded regions 1108 may comprise less than about 30 percent of a total area of the multi-layer sidewall. Furthermore, a color indicator may be disposed within the un-bonded regions or air gaps 1110. Disposing the color indicator within the un-bonded regions or air gaps 1110 provides separations (e.g., distinct portions) of the color indicator.

In still further implementations, the one or more of the layers of the thermoplastic bag can be subjected to SELFing as described in U.S. Pat. Nos. 9,669,595; 5,518,801; 6,139, 185; 6,150,647; 6,394,651; 6,394,652; 6,513,975; 6,695, 476; U.S. Patent Application Publication No. 2004/0134923; and U.S. Patent Application Publication No. 2006/0093766, the entire contents of each of the foregoing patents and patent applications are hereby incorporated by reference.

Figure 12:
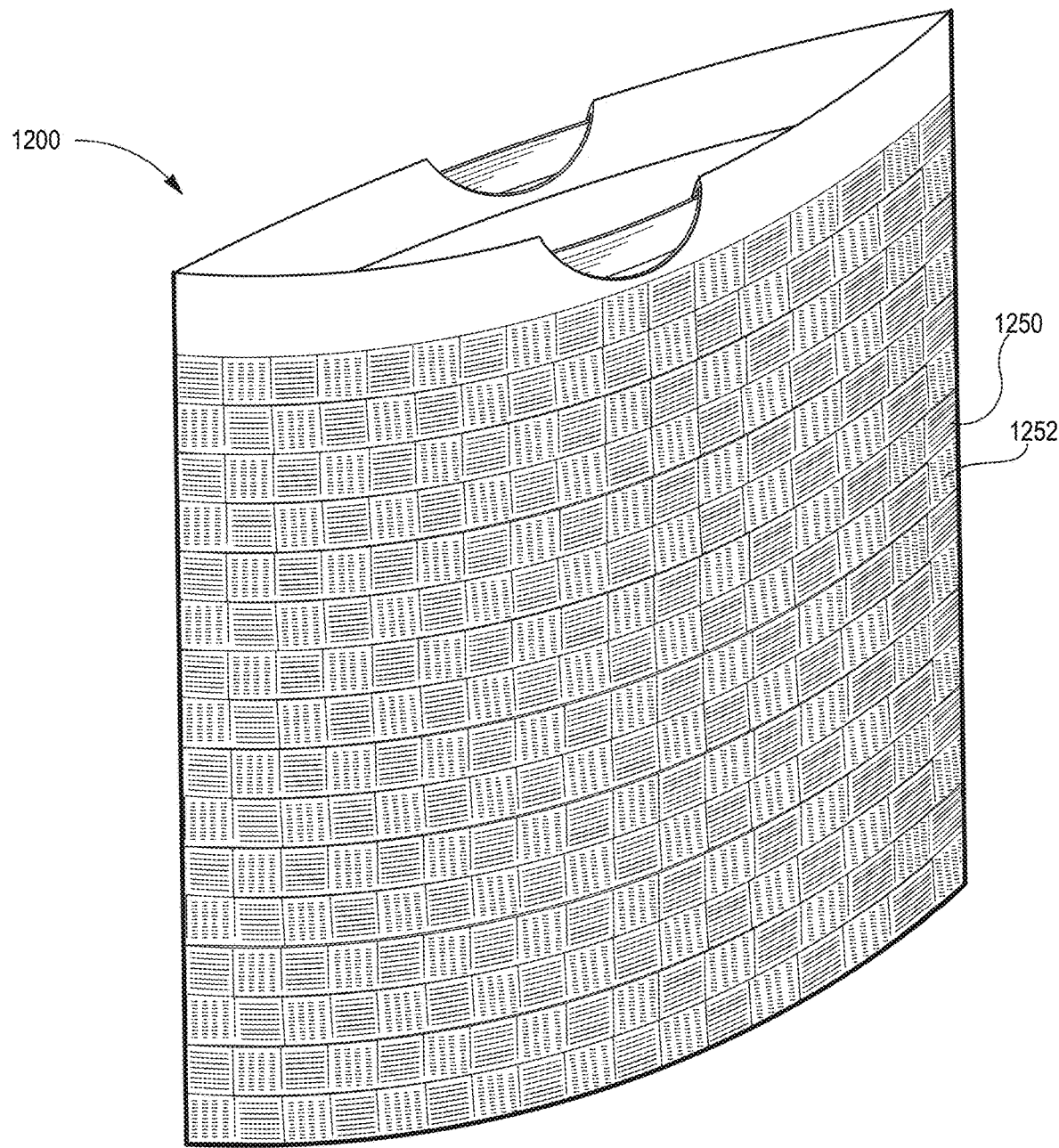
FIG. 12 illustrates a perspective view of thermoplastic bag having another pattern in accordance with one or more embodiments.

FIG. 12 illustrates another thermoplastic bag 1200 similar to the thermoplastic bag 100 albeit with sidewalls that are SELF'ed. The thermoplastic bag 1200 can include the same structure as the thermoplastic bag 1000 (including the color indicator) albeit with a different pattern of intermittent bonds and thinner webs and thicker ribs. In particular, the thermoplastic bag 1200 may include a single pattern of raised like elements arranged in a checkerboard pattern. The pattern can comprise a micro pattern of raised rib-like elements 1252 and a macro pattern of raised rib-like elements 1250. In one or more embodiments, the color indicator is positioned on the macro patterns. In alternate embodiments, the color indicator is positioned on the micro patterns. In still further embodiments, the color indicator is positioned on both the micro and macro patterns.

Figure 13A:
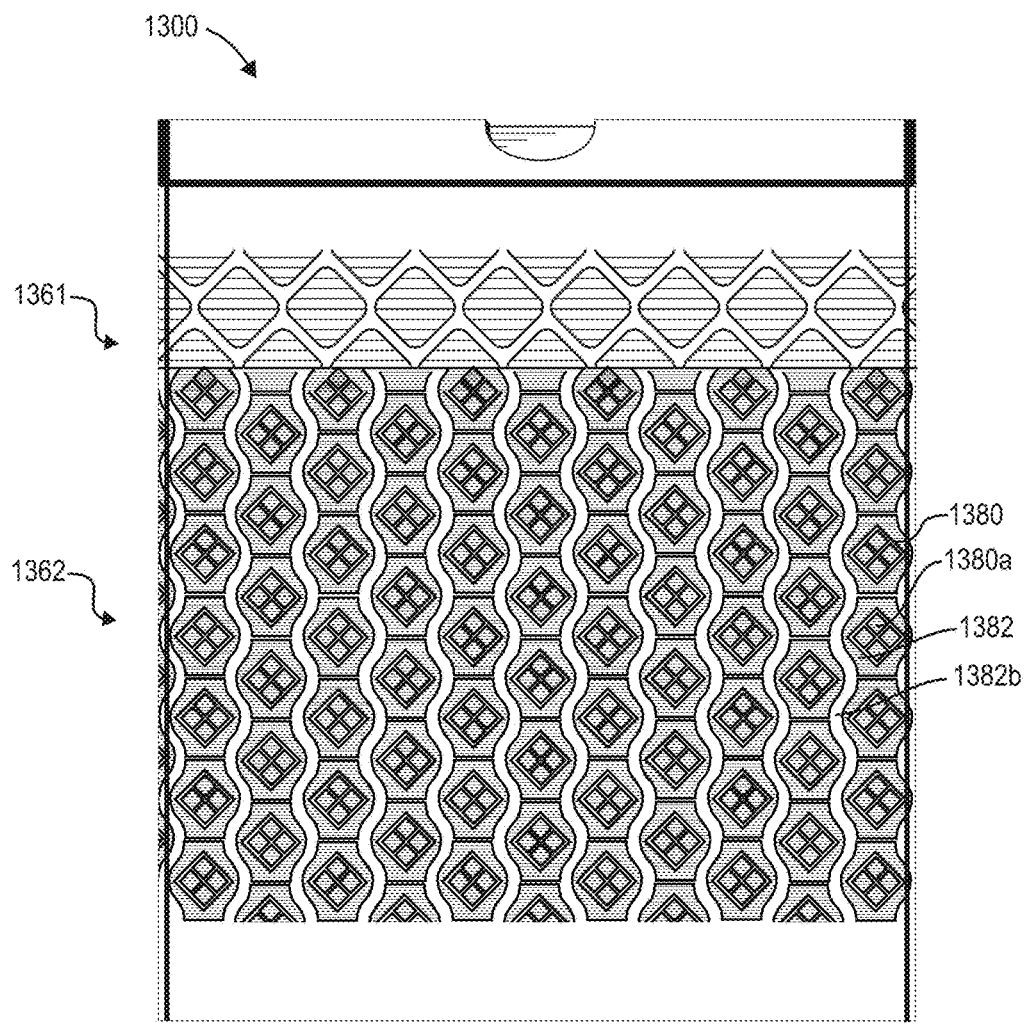
FIGS. 13A-13B illustrate a front view of a thermoplastic bag having yet another pattern in accordance with one or more embodiments.
Figure 13B:
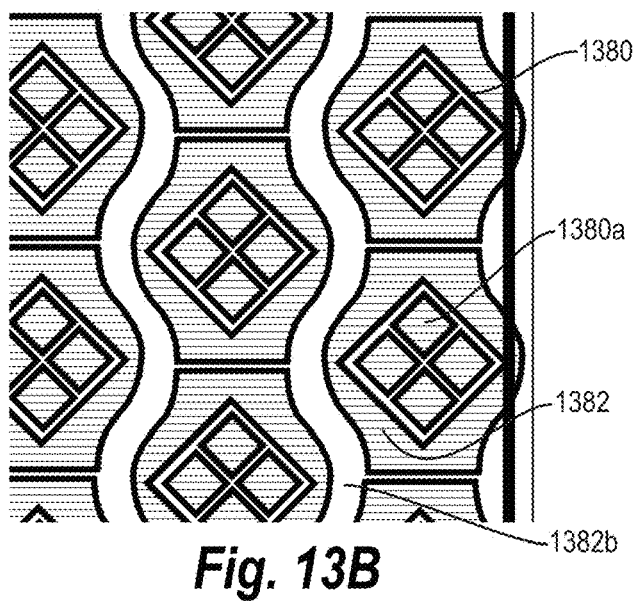

FIG. 13A shows another thermoplastic bag 1300 similar to the thermoplastic bag 100. FIG. 13B is an enlarged view of a portion of the thermoplastic bag 1300. Referring to FIGS. 13A and 13B together, one or more of the sidewalls of the thermoplastic bag 1300 have a first plurality of raised rib-like elements 1382 in a macro pattern (e.g., a bulbous pattern) and a second plurality of raised rib-like elements 1380a in a micro pattern (e.g., four diamonds) in a first middle portion 1362. As shown, the second plurality of raised rib-like elements 1380a in the micro pattern are nested within the macro patterns. Furthermore, the thermoplastic bag 1300 includes web areas 1380, 1382b. The web areas 1380, 1382b can surround the micro and the macro patterns of raised rib-like elements. The plurality of web areas 1380, 1382b comprise areas in which the first layer and the second layer are separated to form intermittent bonding between the layers (i.e., the inner bag and the outer bag). Furthermore, as shown by FIG. 13, the web areas 1382b are arranged in a sinusoidal pattern. In one or more embodiments, the color indicator is positioned on the web areas 1382b.

Additionally, FIGS. 13A and 13B illustrates that the thermoplastic bags described herein can include areas with different patterns. In particular, FIG. 13A illustrates an upper portion 1361 of the thermoplastic bag 1300 including a fenced diamond pattern. The fenced diamond pattern can comprise raised-rib-like elements arranged in diamond patterns where the intersections of the sides of the diamond are rounded rather than ending in corners. The fenced diamond pattern can also comprise areas in which the first layer and the second layer are separated to form intermittent bonding between the layers (i.e., the inner bag and the outer bag). In one or more embodiments, the color indicator is positioned on upper portion 1361.

Figure 14:
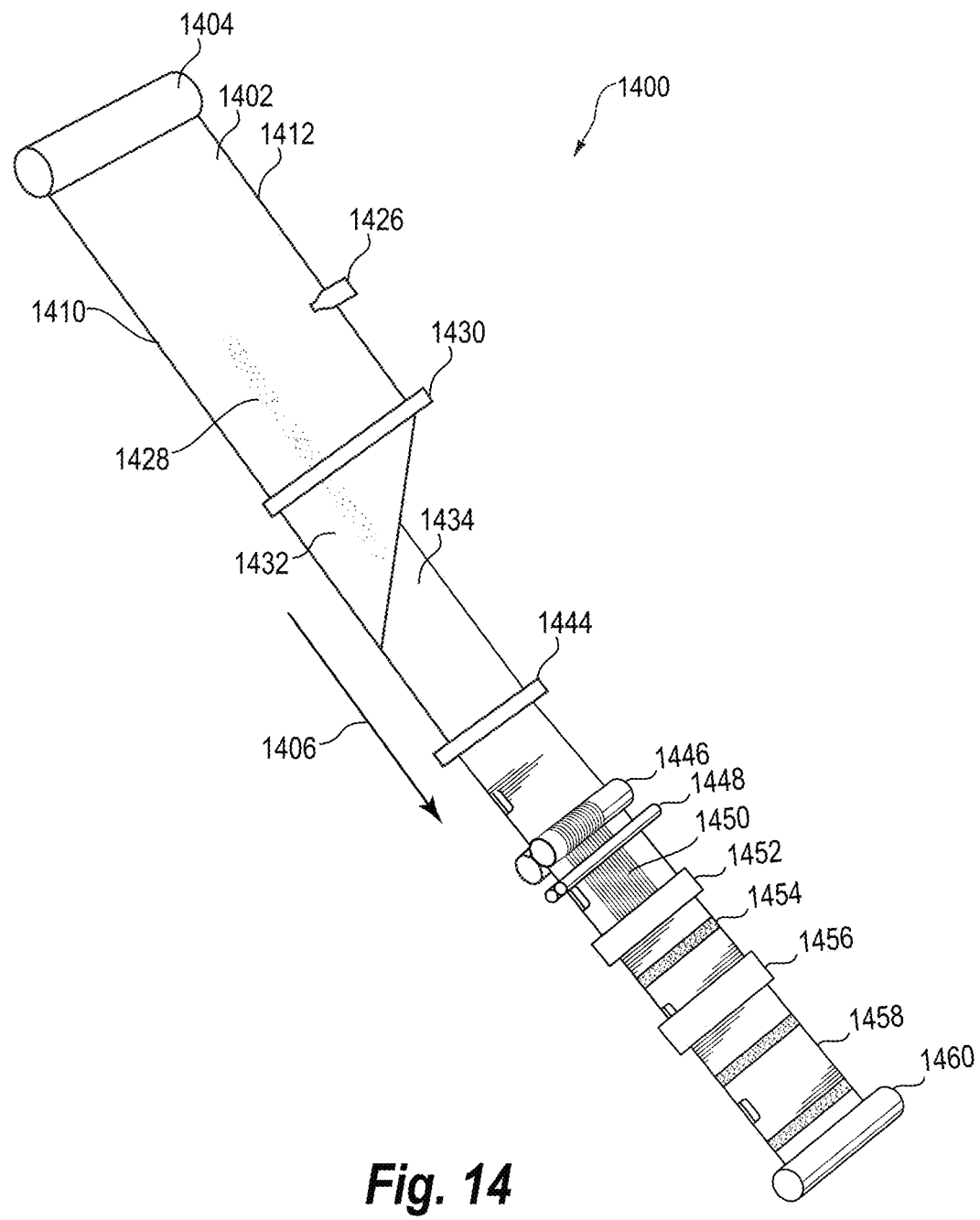
FIG. 14 illustrates a schematic diagram of a manufacturing process for producing thermoplastic bags having a color indicator in accordance with one or more embodiments.
Figure 15:
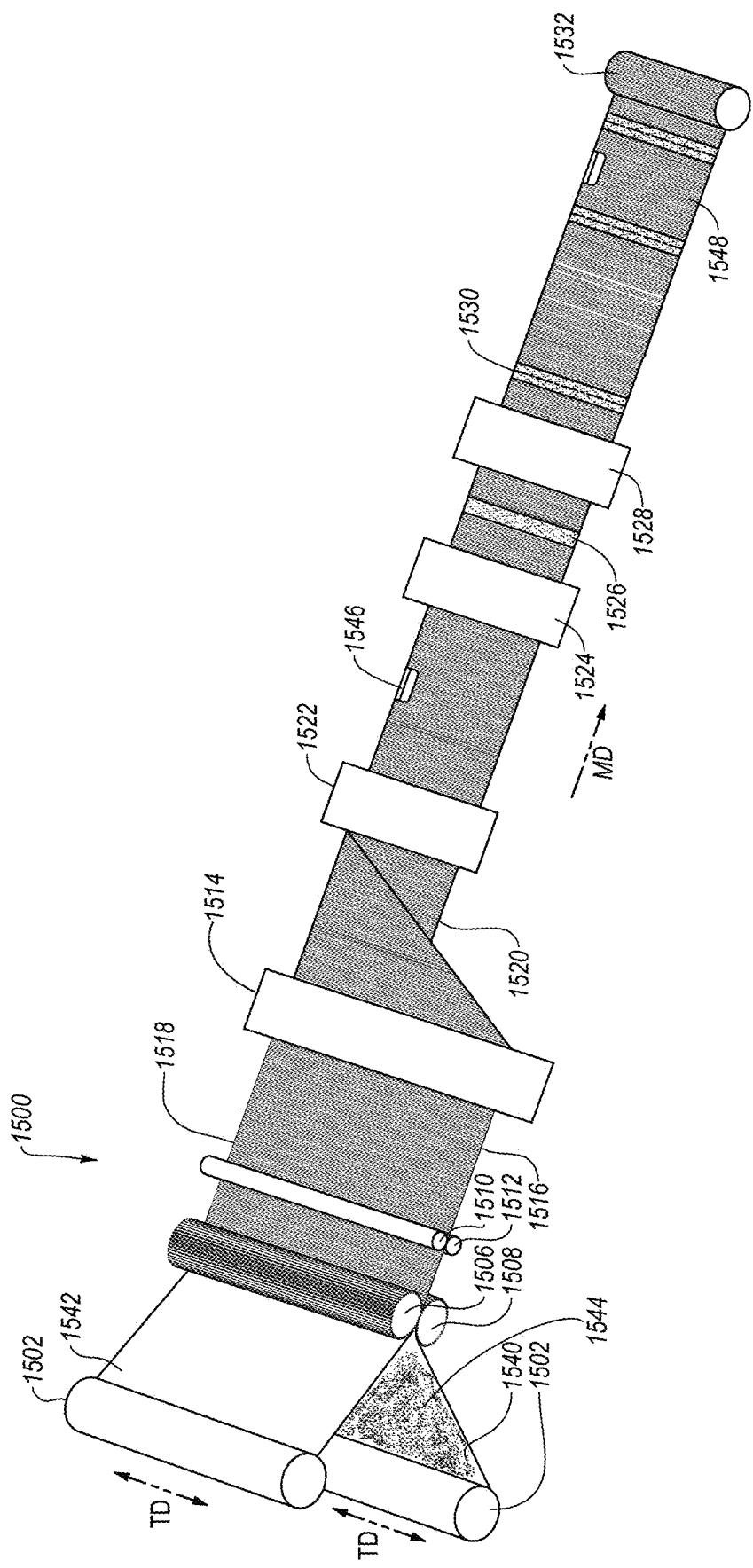
FIG. 15 illustrates a schematic diagram of another manufacturing process for producing thermoplastic bags having a color indicator in accordance with one or more embodiments.

One or more implementations of the present invention can also include methods of forming thermoplastic bags. FIGS. 14-15 and the accompanying description describe such methods. Of course, as a preliminary matter, one of ordinary skill in the art will recognize that the methods explained in detail herein can be modified. For example, various acts of the method described can be omitted or expanded, additional acts can be included, and the order of the various acts of the method described can be altered as desired.

Referring to FIG. 14, a schematic of an implementation for high-speed automated manufacturing of bags process 1400 is shown. In the illustrated implementation, the process 1400 may begin by unwinding a web 1402 of thermoplastic sheet material from a roll 1404 and advancing the web along a machine direction 1406. The unwound web 1402 may have a rectangular profile including a width that is perpendicular to the machine direction 1406 as measured between a first edge 1410 and an opposite second edge 1412. In other manufacturing environments, the process may involve extruding the web 1402 using a thermoplastic production process.

After unwinding the web 1402, the process 1400 can involve dispensing a substance 1428 containing a color indicator using a dispenser 1426. In one or more embodiments, the substance 1428 is additionally, or alternatively, applied using a roller or a slot cast. In one or more embodiments, the substance 1428 includes a liquid application, a powder application or any other application discussed above. As mentioned above, the process 1400 can be modified so that the act of applying the substance containing the color indicator can occur earlier or later than what is shown in FIG. 14. For example, in one or more embodiments, the substance 1428 containing the color indicator (or the color indicator itself) can be coextruded with the web 1402 using the thermoplastic production process.

Subsequently, the process 1400 can include a folding process 1430 that involves folding the web 1402 about its width and in-line with the machine direction 1406 to provide adjacent first and second folded halves 1432, 1434. The folding of the web 1402 may cause the second edge 1412 to move adjacent to the first edge 1410 such that the two edges correspond to the opened top edge of the finished bag. The mid-width portion of the web 1402 may correspond to the reinforced bottom edge portion of the finished bag which may move in parallel with the machine direction 1406. Additionally, the folded halves 1432, 1434 of the web 1402 correspond to the first and second sidewalls of the finished bag.

Additional processing steps may be applied to produce the finished bag. In particular, the process 1400 can include a draw tape insertion process 1444 that involves inserting a draw tape into the first edge 1410 and the second edge 1412 of the web 1402.

Optionally, to bond (and optionally stretch) the halves of the web, the processing equipment may include a pair of intermeshing rollers 1446 such as those described herein above. The folded halves 1432, 1434 may be advanced along the machine direction 1406 between the intermeshing rollers 1446, which may be set into rotation in opposite rotational directions to impart the resulting bonding pattern 1450. To facilitate patterning of the folded halves 1432, 1434, the intermeshing rollers 1446 may be forced or directed against each other by, for example, hydraulic actuators. The pressure at which the rollers are pressed together may be in a first range from 30 PSI (2.04 atm) to 100 PSI (6.8 atm), a second range from 60 PSI (4.08 atm) to 90 PSI (6.12 atm), and a third range from 75 PSI (5.10 atm) to 85 PSI (5.78 atm). In one or more implementations, the pressure may be about 80 PSI (5.44 atm).

In the illustrated implementation, the intermeshing rollers 1446 may be arranged so that they are co-extensive with or wider than the width of the folded halves 1432, 1434. In one or more implementations, the bonding pattern 1450 created by intermeshing rollers 1446 may extend from proximate the folded edge to the adjacent edges 1410, 1412. To avoid imparting the bonding pattern 1450 onto the portion of the folded halves 1432, 1434 that includes the draw tape, the corresponding ends of the intermeshing rollers 1446 may be smooth and without the ridges and grooves. Thus, the adjacent edges 1410, 1412 and the corresponding portion of the folded halves 1432, 1434 proximate those edges that pass between the smooth ends of the intermeshing rollers 1446 may not be imparted with the bonding pattern 1450.

The processing equipment may include pinch rollers 1448 to accommodate the width of the folded halves 1432, 1434. To produce the finished bag, the processing equipment may further process the folded halves 1432, 1434. For example, to form the parallel side edges of the finished bag, the folded halves 1432, 1434 may proceed through a sealing operation 1452 in which heat seals 1454 may be formed between the folded edge and the adjacent edges 1410, 1412. The heat seals may fuse together the adjacent folded halves 1432, 1434. The heat seals 1454 may be spaced apart along the folded halves 1432, 1434 and in conjunction with the folded outer edge may define individual bags. The heat seals 1454 may be made with a heating device, such as, a heated knife or a sealing bars as described in greater detail below. A perforating operation 1456 may perforate the heat seals 1454 with a perforating device, such as, a perforating knife so that individual bags 1458 may be separated from the web 1402. In one or more implementations, the folded halves 1432, 1434 may be folded one or more times before the folded halves 1432, 1434 may be directed through the perforating operation. The folded halves 1432, 1434 embodying the individual bags 1458 may be wound into a roll 1460 for packaging and distribution. For example, the roll 1460 may be placed in a box or a bag for sale to a customer.

In one or more implementations of the process 1400, a cutting operation may replace the perforating operation 1456. The web is directed through a cutting operation which cuts the folded halves 1432, 1434 at location into individual bags 1458 prior to winding onto a roll 1460 for packaging and distribution. For example, the roll 1460 may be placed in a box or bag for sale to a customer. The bags may be interleaved prior to winding into the roll 1460. In one or more implementations, the folded halves 1432, 1434 may be folded one or more times before the folded web is cut into individual bags. In one or more implementations, the individual bags 1458 may be positioned in a box or bag, and not onto the roll 1460.

FIG. 15 illustrates an exemplary embodiment of a manufacturing process for making multi-layer thermoplastic film (e.g., the first and second films 1540, 1542) having the color indicator 1544 (e.g., a substance containing the color indicator 1544) disposed therein and then producing multi-layer thermoplastic bags therefrom. According to the process 1500, a first film 1540 and a second film 1542 may be unwound from stock rolls 1502, respectively, and directed along a machine direction MD. Alternatively, the first and second films 1540, 1542 may be extruded directly from one or more extrusion towers rather than stock rolls 1502.

The color indicator 1544 (e.g., one or more substances containing the color indicator 1544) may be applied to one or more of the first and second films 1540, 1542 on the inner sides of the first and second films 1540, 1542 (e.g., the sides of the first and second films 1540, 1542 that will be bonded together) prior to bonding the first and second films 1540, 1542. The color indicator 1544 may be applied through one or more of laminating, dusting, spraying, rolling, and any other method known in the art for applying substances to films. In one or more embodiments, the color indicator 1544 (or a substance containing the color indicator 1544) is coextruded with the first and second films 1540, 1542.

After the color indicator 1544 has been applied to one or more of the first and second films 1540, 1542, the first and second films 1540, 1542 may be passed between a pair of cylindrical intermeshing rollers 1506, 1508 to incrementally stretch and lightly laminate the initially separate first and second films 1540, 1542 to create un-bonded regions and bonded regions in at least one section of a multi-layer film (i.e., eventual sidewall of the multi-layer bag). The intermeshing rollers 1506, 1508 shown in FIG. 15 may have a construction similar to that of any of the intermeshing rollers described in U.S. Pat. No. 8,603,609. The rollers 1506, 1508 may be oriented such that longitudinal axes of the rollers are perpendicular to the machine direction. Additionally, the rollers 1506, 1508 may rotate about their longitudinal axes in opposite rotational directions. In some embodiments, motors may be provided to power rotation of the rollers 1506, 1508 in a controlled manner. As the first and second films 1540, 1542 pass between the pair of rollers 1506, 1508, the ridges and/or teeth of the rollers 1506, 1508 can form the multi-layer film (i.e., eventual sidewall of the multi-layer bag).

During the manufacturing process 1500, the multi-layer film can also pass through a pair of pinch rollers 1510, 1512. The pinch rollers 1510, 1512 can be appropriately arranged to grasp the multi-layer film.

A folding operation 1514 can fold the multi-layer film to produce the sidewalls of the finished bag. The folding operation 1514 can fold the multi-layer film in half along the transverse direction. In particular, the folding operation 1514 can move a first edge 1516 adjacent to the second edge 1518, thereby creating a folded edge 1520. For example, the process may include the folding operation described in U.S. Pat. No. 8,568,283, the entire contents of which are hereby incorporated by reference in their entirety. Additionally, the folding operation 1514 may form a hem at an eventual top portion of a thermoplastic film.

To produce the finished bag, the processing equipment may further process the folded multi-layer film. In particular, a draw tape operation 1522 can insert a draw tape 1546 into the first edge 1516 and the second edge 1518 of the multi-layer film. Furthermore, a sealing operation 1524 can form the parallel side edges of the finished bag by forming heat seals 1526 between adjacent portions of the folded multi-layer lightly-laminated film. Moreover, the sealing operation 1524 can seal the hem to a sidewall of the eventual thermoplastic bag. The heat seal 1526 may strongly bond adjacent layers together in the location of the heat seal 1526 so as to tightly seal the edges (e.g., produce an at least substantially water tight seal) of the finished bag. The heat seals 1526 may be spaced apart along the folded multi-layer film to provide a desired width to the finished bags. The sealing operation 1524 can form the heat seals 1526 using a heating device, such as, a heated knife.

A perforating operation 1528 may form a perforation 1530 in the heat seals 1526 using a perforating device, such as, a perforating knife. The perforations 1530 in conjunction with the folded outer edge 1520 can define individual bags 1548 that may be separated from the multi-layer film. A roll 1532 can wind the multi-layer lightly-laminated film embodying the finished individual bags 1548 for packaging and distribution. For example, the roll 1532 may be placed into a box or bag for sale to a customer.

In still further implementations, the folded multi-layer lightly-laminated film may be cut into individual bags along the heat seals 1526 by a cutting operation. In another implementation, the folded multi-layer lightly-laminated film may be folded one or more times prior to the cutting operation. In yet another implementation, the side sealing operation 1524 may be combined with the cutting and/or perforation operations 1528.

In further embodiments, the hem of the thermoplastic bag may be ring rolled and/or SELF'd to form a pattern in the hem. Moreover, the hem of the thermoplastic bag may be ring rolled and/or SELF'd prior to being folded into a hem shape and/or after being folded into a hem shape.

One will appreciate in view of the disclosure herein that the process 1500 described in relation to FIG. 15 can be modified to omit or expanded acts, or vary the order of the various acts as desired. In particular, the process 1500 can involve placing or applying a color indicator such that the color indicator is positioned in or around the hem as described below.

The present disclosure may be embodied in other specific forms without departing from its spirit or essential characteristics. For example, the illustrated and described implementations involve non-continuous (i.e., discontinuous or partially discontinuous lamination) to provide the weak bonds. In alternative implementations, the lamination may be continuous. For example, multi film layers could be coextruded so that the layers have a bond strength that provides for delamination prior to film failure to provide similar benefits to those described above. Thus, the described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

What is claimed is:

1. A film, comprising:
   a first layer of thermoplastic material;
   a first color indicator applied to the first layer of thermoplastic material, wherein the first color indicator is configured to change a color appearance of the first color indicator from a first color to a second color in response to exposure to a first set of malodor particles; and
   a second color indicator applied to the first layer of thermoplastic material, wherein the second color indicator is configured to change a color appearance of the second color indicator from the first color to a third color in response to exposure to a second set of malodor particles that is different than the first set of malodor particles.

2. The film of claim 1, wherein the first color indicator is configured to change the color appearance of the first color indicator from the first color to the second color by:
   transitioning the color appearance of the first color indicator partially to the second color in response to exposure to malodor particles from the first set of malodor particles; and
   transitioning the color appearance of the first color indicator completely to the second color in response to exposure to additional malodor particles from the first set of malodor particles subsequent to transitioning partially to the second color.

3. The film of claim 2, wherein the first color indicator is configured to change the color appearance of the first color indicator from the first color to the second color by changing the color appearance of the first color indicator from the first color to a clear appearance.

4. The film of claim 1, wherein:
   the first color indicator is configured to change the color appearance of the first color indicator in response to exposure to the first set of malodor particles having a first chemical structure; and
   the second color indicator is configured to change the color appearance of the second color indicator in response to exposure to the second set of malodor particles having a second chemical structure that is different than the first chemical structure.

5. The film of claim 4, wherein:
   the first color indicator is configured to change the color appearance of the first color indicator in response to exposure to the first set of malodor particles having the first chemical structure giving the first set of malodor particles a first pH value; and
   the second color indicator is configured to change the color appearance of the second color indicator in response to exposure to the second set of malodor particles having the second chemical structure giving the second set of malodor particles a second pH value.

6. The film of claim 1, further comprising an odor control component applied to the first layer of thermoplastic material, wherein a rate of change of the color appearance of the first color indicator is controlled based on one or more of a chemistry of the odor control component or a concentration of the odor control component.

7. The film of claim 1, wherein the first color indicator is applied as a pattern onto a surface of the first layer of thermoplastic material.

8. The film of claim 1, wherein the first color indicator covers a surface of the first layer of thermoplastic material.

9. The film of claim 1, wherein:
the first layer of thermoplastic material is formed into a thermoplastic bag; and
the first color indicator is applied within a hem of the thermoplastic bag.

10. The film of claim 1, further comprising a second layer of thermoplastic material adjacent to the first layer of thermoplastic material, wherein the first color indicator is disposed on the first layer of thermoplastic material and between the first layer of thermoplastic material and the second layer of thermoplastic material.

11. The film of claim 1, wherein the first color indicator is embedded within the first layer of thermoplastic material.

12. A thermoplastic bag, comprising:
a first sidewall;
a second sidewall opposite the first sidewall and joined with the first sidewall along a first side edge, an opposite second side edge, and a bottom edge;
a first color indicator applied to at least one of the first sidewall or the second sidewall, wherein the first color indicator is configured to change a color appearance of the first color indicator from a first color to a second color in response to exposure to a first set of malodor particles; and
a second color indicator applied to at least one of the first sidewall or the second sidewall, wherein the second color indicator is configured to change a color appearance of the second color indicator from the first color to a third color in response to exposure to a second set of malodor particles that is different than the first set of malodor particles.

13. The thermoplastic bag of claim 12, wherein:
the first color indicator is configured to change the color appearance of the first color indicator in response to exposure to the first set of malodor particles having a first chemical structure; and
the second color indicator is configured to change the color appearance of the second color indicator in response to exposure to the second set of malodor particles having a second chemical structure that is different than the first chemical structure.

14. The thermoplastic bag of claim 13, wherein:
the first color indicator is configured to change the color appearance of the first color indicator in response to exposure to the first set of malodor particles having the first chemical structure giving the first set of malodor particles a first pH value; and
the second color indicator is configured to change the color appearance of the second color indicator in response to exposure to the second set of malodor particles having the second chemical structure giving the second set of malodor particles a second pH value.

15. The thermoplastic bag of claim 14, further comprising an odor control component applied to at least one of the first sidewall or the second sidewall, wherein a rate of change of the color appearance of the first color indicator is configured based on one or more of a chemistry of the odor control component or a concentration of the odor control component.

16. The thermoplastic bag of claim 12, wherein the first color indicator is embedded within at least the one of the first sidewall or the second sidewall.

17. The thermoplastic bag of claim 12, wherein at least one of the first sidewall or the second sidewall comprises a first film of thermoplastic material and a second film of thermoplastic material, and the first color indicator is disposed between the first film of thermoplastic material and the second film of thermoplastic material.

18. A method of manufacturing thermoplastic bags having color indicators, comprising:
providing a thermoplastic film;
applying a first color indicator to the thermoplastic film, wherein the first color indicator is configured to change a color appearance of the first color indicator from a first color to a second color in response to exposure to a first set of malodor particles;
applying a second color indicator to the thermoplastic film, wherein the second color indicator is configured to change a color appearance of the second color indicator from the first color to a third color in response to exposure to a second set of malodor particles that is different than the first set of malodor particles; and
forming the thermoplastic film into a bag.

19. The method of claim 18, wherein:
the first color indicator is configured to change the color appearance of the first color indicator in response to exposure to the first set of malodor particles having a first chemical structure; and
the second color indicator is configured to change the color appearance of the second color indicator in response to exposure to the second set of malodor particles having a second chemical structure that is different than the first chemical structure.

20. The method of claim 18, wherein applying the first color indicator to the thermoplastic film comprises embedding the first color indicator as an additive into the thermoplastic film during an extrusion process.

* * * * *